US010603884B2

(12) United States Patent
Hoenigmann

(10) Patent No.: US 10,603,884 B2
(45) Date of Patent: Mar. 31, 2020

(54) MULTI-LAYER FILM

(71) Applicant: Berry Plastics Corporation, Evansville, IN (US)

(72) Inventor: Martin F. Hoenigmann, Chippewa Falls, WI (US)

(73) Assignee: Berry Plastics Corporation, Evansville, IN (US)

( * ) Notice: Subject to any disclaimer, the term of this patent is extended or adjusted under 35 U.S.C. 154(b) by 0 days.

(21) Appl. No.: 15/643,982

(22) Filed: Jul. 7, 2017

(65) Prior Publication Data

US 2018/0009205 A1 Jan. 11, 2018

Related U.S. Application Data

(60) Provisional application No. 62/359,439, filed on Jul. 7, 2016.

(51) Int. Cl.
*B65D 27/32* (2006.01)
*B65D 75/20* (2006.01)
(Continued)

(52) U.S. Cl.
CPC ........ *B32B 27/32* (2013.01); *A61F 13/55105* (2013.01); *B32B 7/04* (2013.01); *B32B 25/08* (2013.01); *B32B 25/16* (2013.01); *B32B 27/08* (2013.01); *B32B 27/18* (2013.01); *B32B 27/306* (2013.01); *B32B 27/327* (2013.01); *B32B 37/06* (2013.01); *B65B 9/06* (2013.01); *B65B 9/08* (2013.01); *B65B 51/10* (2013.01); *B65B 51/30* (2013.01); *B65D 65/38* (2013.01); *B65D 75/06* (2013.01); *B65D 75/20* (2013.01); *B65D 75/30* (2013.01); *B32B 2250/03* (2013.01); *B32B 2250/05* (2013.01); *B32B 2250/242* (2013.01); *B32B 2270/00* (2013.01); *B32B 2307/31* (2013.01); *B32B 2307/4026* (2013.01); *B32B 2307/50* (2013.01); *B32B 2307/54* (2013.01); *B32B 2307/558* (2013.01); *B32B 2307/5825* (2013.01); *B32B 2307/718* (2013.01); *B32B 2307/72* (2013.01); *B32B 2307/732* (2013.01);
(Continued)

(58) Field of Classification Search
CPC .............................. B32B 27/32; B32B 27/327
See application file for complete search history.

(56) References Cited

U.S. PATENT DOCUMENTS 3,958,749 A 5/1976 Goodrich
4,472,468 A 9/1984 Tailor
(Continued)

FOREIGN PATENT DOCUMENTS

WO 2007095667 9/2008
WO 2015057501 A1 4/2015
WO 2015123829 A1 8/2015

OTHER PUBLICATIONS

International (PCT) Search Report and Written Opinion for PCT/US17/35292 dated Aug. 29, 2017, BP-504 PCT ||, 14 pages.
(Continued)

*Primary Examiner* — Jes F Pascua
*Assistant Examiner* — Nina K Attel
(74) *Attorney, Agent, or Firm* — Barnes & Thornburg LLP

(57) ABSTRACT

A multi-layer film includes a first-seal layer and a second-seal layer. The multi-layer film may be used to form a package for consumer-care products.

16 Claims, 6 Drawing Sheets

18 32 28 30 33 22 20 12 10 14 16 24 26 31

(51) Int. Cl.

| | |
|---|---|
| ***B65D 75/30*** | (2006.01) |
| ***B32B 27/32*** | (2006.01) |
| ***B65B 9/08*** | (2012.01) |
| ***B32B 25/08*** | (2006.01) |
| ***B32B 27/08*** | (2006.01) |
| ***B32B 25/16*** | (2006.01) |
| ***B32B 27/18*** | (2006.01) |
| ***B65B 9/06*** | (2012.01) |
| ***B65D 75/06*** | (2006.01) |
| ***B32B 7/04*** | (2019.01) |
| ***B65B 51/30*** | (2006.01) |
| ***B32B 27/30*** | (2006.01) |
| ***A61F 13/551*** | (2006.01) |
| ***B32B 37/06*** | (2006.01) |
| ***B65B 51/10*** | (2006.01) |
| ***B65D 65/38*** | (2006.01) |

(52) U.S. Cl.

CPC ... *B32B 2307/744* (2013.01); *B32B 2323/046* (2013.01); *B32B 2439/00* (2013.01); *B32B 2553/00* (2013.01); *B32B 2555/02* (2013.01)

(56) References Cited

U.S. PATENT DOCUMENTS

| | | | | |
|---|---|---|---|---|
| 4,731,273 | A | 3/1988 | Bonk | |
| 5,158,815 | A | 10/1992 | Doheny | |
| 5,397,615 | A | 3/1995 | Van Beersel | |
| 5,749,202 | A | 5/1998 | Eichbauer | |
| 5,752,362 | A | 5/1998 | Eichbauer | |
| 5,759,648 | A | 6/1998 | Idlas | |
| 5,814,399 | A | 9/1998 | Eichbauer | |
| 5,902,684 | A | 5/1999 | Bullard | |
| 6,015,235 | A | 1/2000 | Kraimer | |
| 6,206,569 | B1 | 3/2001 | Kraimer | |
| 6,582,828 | B1 | 6/2003 | Kaschel | |
| RE38,429 | E | 2/2004 | Eichbauer | |
| 6,977,113 | B2 | 12/2005 | Kody | |
| 7,052,772 | B2 | 5/2006 | Lottes | |
| 7,235,607 | B2 | 6/2007 | Ohlsson | |
| 7,622,406 | B2 | 11/2009 | Holland | |
| 7,820,570 | B2 | 10/2010 | Holland | |
| 7,828,029 | B2 | 11/2010 | Holland | |
| 8,709,595 | B2 | 4/2014 | Siegel | |
| 8,999,513 | B2 | 4/2015 | Custodero | |
| 9,040,151 | B2 | 5/2015 | Pavlik | |
| 9,126,269 | B2 | 9/2015 | Ohlsson | |
| 2001/0046606 | A1 | 11/2001 | Tau | |
| 2003/0049479 | A1 | 3/2003 | Quintin | |
| 2006/0127657 | A1* | 6/2006 | Pettis | B32B 25/08 428/213 |
| 2006/0183860 | A1 | 8/2006 | Mehta | |
| 2006/0188678 | A1 | 8/2006 | Ohlsson | |
| 2010/0151218 | A1 | 6/2010 | Curie | |
| 2010/0249327 | A1 | 9/2010 | Leland | |
| 2011/0244206 | A1 | 10/2011 | Penache | |
| 2012/0100356 | A1 | 4/2012 | Ohlsson | |
| 2012/0240511 | A1 | 9/2012 | Engelhard | |
| 2013/0168958 | A1 | 7/2013 | Van Den Bergh | |
| 2014/0370278 | A1 | 12/2014 | Hausmann | |
| 2015/0344741 | A1* | 12/2015 | Blackwell | C09J 7/38 156/60 |
| 2016/0244229 | A1* | 8/2016 | Lai | B32B 7/02 |

OTHER PUBLICATIONS

Office Action dated Jun. 14, 2018 for US App. No. for U.S. Appl. No. 15/334,991 (pp. 1-10).

International (PCT) Search Report and Written Opinion for PCT/US17/41082 dated Dec. 4, 2017, BP-505 PCT ||, 15 pages.

International (PCT) Search Report for PCT/US16/58892 dated Jan. 24, 2017, BP-401 PCT ||, 8 pages.

Office Action dated Jan. 22, 2019 for U.S. Appl. No. 15/334,991, BP-488 US-U ||, (pp. 1-10).

Applied Plastics Engineering Handbook, 1st edition, edited by Myer Kutz, published Jul. 20, 2011, 2 pages.

* cited by examiner

MULTI-LAYER FILM

CROSS REFERENCE TO RELATED APPLICATIONS

This application claims priority under 35 U.S.C. § 119(e) to U.S. Provisional Patent Application No. 62/359,439, filed Jul. 7, 2016, which is expressly incorporated by reference herein.

BACKGROUND

The present disclosure relates to multi-layer films, and particularly to films for use in packaging. More particularly, the present disclosure relates to packaging used for consumer-care products.

SUMMARY

According to the present disclosure, a multi-layer film is used to form a bag for holding consumer-care products therein. The multi-layer film includes a first-seal layer and a second-seal layer. The second-seal layer is arranged to define an interior product-storage region in the bag. The first-seal layer is arranged to surround and locate the second-seal layer between the interior product-storage region and the first-seal layer.

In illustrative embodiments, the multi-layer film further includes a deformation-resistant layer. The deformation-resistant layer extends between and interconnects the first-seal layer and the second-seal layer. The deformation-resistant layer is configured to minimize deformation of the multi-layer film during handling of the package so that the outer surface of the package remains uninterrupted.

In illustrative embodiments, the deformation-resistant layer comprises a polypropylene impact copolymer material. In illustrative embodiments, the deformation-resistant layer comprises up to about 90% by weight polypropylene impact copolymer material.

In illustrative embodiments, the deformation-resistant layer comprises a metallocene LLDPE (mLLDPE) material. In illustrative embodiments, the deformation-resistant layer comprises up to about 60% by weight mLLDPE material.

In illustrative embodiments, a package is formed using the multi-layer film. The package includes a first closure formed by heat-sealing a first end of the bag. The multi-layer film is configured to maximize heat-seal strength at the first closure so that the multi-layer film fails at a location other than the first closure in response to application of force to the first closure. In illustrative embodiments, the heat seal temperature range is about 270° F. to about 400° F. In some illustrative embodiments, the heat seal strength is in a range of about 800 g to about 1,700 g Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
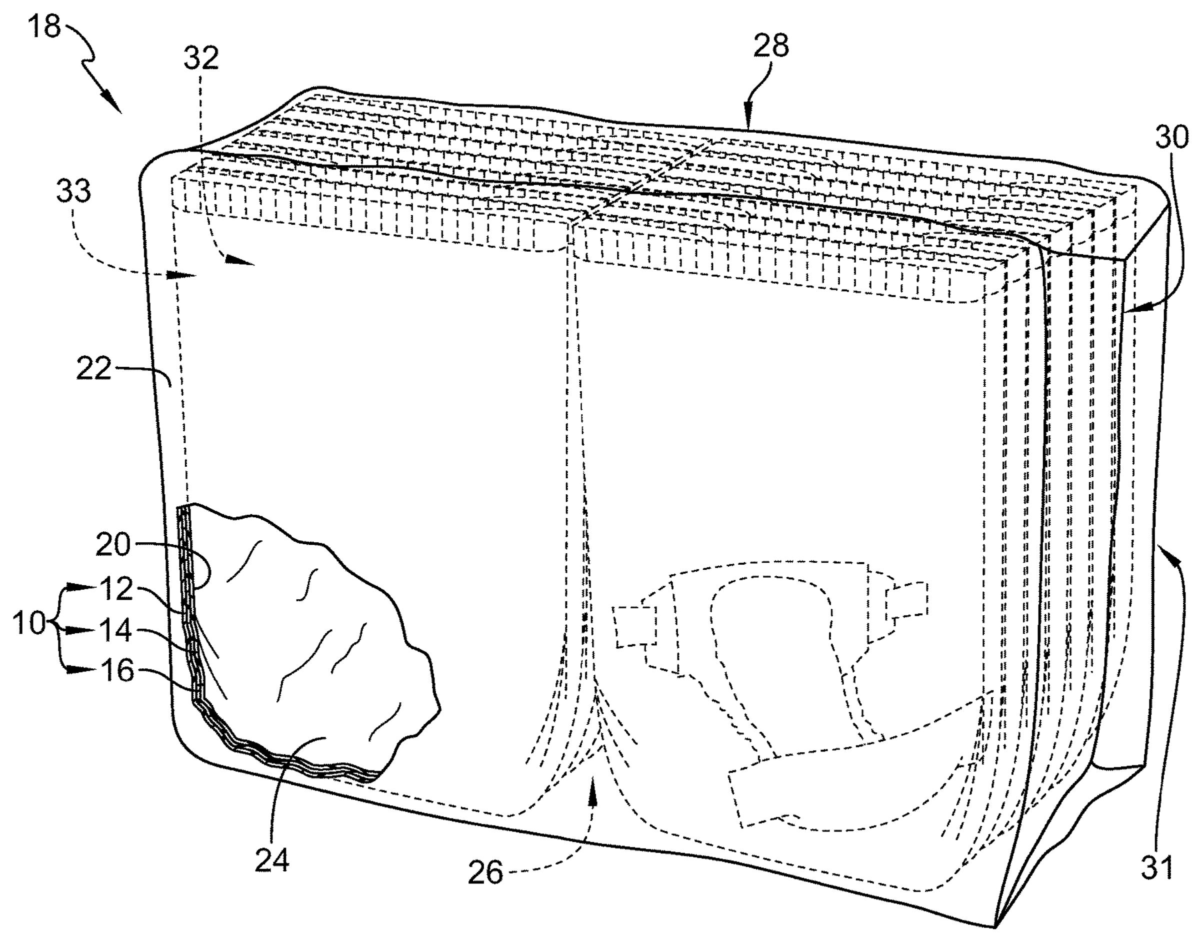
FIG. 1 is a perspective view of a package made from a multi-layer film in accordance with the present disclosure showing that the package includes a bag formed to include an interior product storage region and a sealed first closure, and further showing the multi-layer film includes, in order from outside to inside, a first-seal layer, a deformation-resistant layer, and a second-seal layer.

A first embodiment of a multi-layer film 10 in accordance with the present disclosure is shown, for example, in FIG. 1. Multi-layer film 10 may be formed into a package 18 as shown in FIG. 1 to hold consumer-care products 24 in an interior product-storage region 26 formed in package 18. Multi-layer film 10 resists deformation during handling of package 18 so that an exterior surface 22 of package 18 remains uninterrupted.

Figure 2:
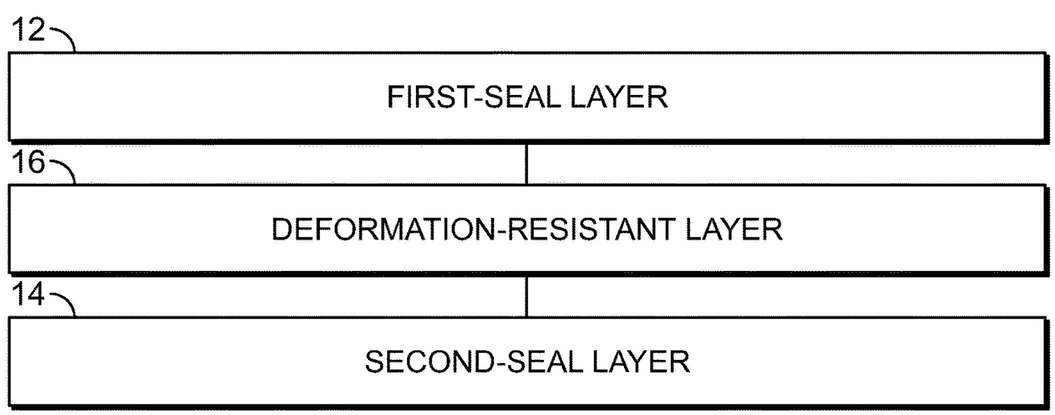
FIG. 2 is a diagrammatic view of the multi-layer film used to form the package of FIG. 1, showing that the multi-layer film includes, from top to bottom, a first-seal layer, a deformation-resistant layer, and a second-seal layer.

Multi-layer film 10 includes a first-seal layer 12, a second-seal layer 14, and a deformation-resistant layer 16 as shown in FIGS. 1 and 2. First-seal layer 12 is located in spaced-apart relation to second-seal layer 14. Deformation-resistant layer 16 extends between and interconnects first-seal layer 12 and second-seal layer 14. First-seal layer 12, second-seal layer 14, and deformation-resistant layer 16 cooperate to minimize deformation of multi-layer film 10 during handling of package 18.

Multi-layer film 10, in one example, may be used to form package 18, as shown in FIG. 1. Package 18 includes a bag 28 configured to hold a consumer-care product 24, a first closure 30, and a second closure 32 located in spaced-apart relation to first closure 30. Illustratively, bag 28 may be wrapped tightly around consumer-care product 24 and require seals at first and second closures 30, 32 having sufficient strength to maintain consumer-care product 24 in compression. Package 18, made from multi-layer film 10, resists deformation during handling of package 18 so that an exterior surface 22 of package 18 remains uninterrupted. In one example, deformation may occur because of a user grasping a heavy package 18. In one example, package 18 may be used to hold consumer-care products as suggested in FIG. 1. Consumer-care products may include, for example, diapers, feminine care products, adult incontinence products, toilet paper, paper towels, and any other suitable or desired products.

Multi-layer film 10 is, for example, a co-extruded film in which first-seal layer 12, second-seal layer 14, and deformation-resistant layer 16 each comprise a composition. In some examples first-seal layer 12 and second seal layer 14 comprises the same composition. In some examples, each composition may be formed by an extrusion process of a formulation.

Illustratively, each formulation of first-seal layer 12, second-seal layer 14, or deformation-resistant layer 16 may be added to a hopper on an extrusion machine and heated to produce a molten material in an extruder. The molten material of each of first-seal layer 12, second-seal layer 14, and deformation-resistant layer 16 may be co-extruded to produce multi-layer film 10. In some examples, first-seal layer 12 and second-seal layer 14 comprise the same formulation.

The compositions of each layer 12, 14, 16 may comprise, for example, a plastic polymer, a material, or a resin, and may optionally include one or more additives. Examples of plastic polymers, resins, or materials suitable for multi-layer film 10 include polyolefins such as high-density polyethylenes (HDPE), low-density polyethylenes (LDPE), and polypropylenes (PP).

In some embodiments, the polyethylene may be a polyethylene homopolymer, a polyethylene copolymer, an enhanced polyethylene, a low-density polyethylene (LDPE), an LDPE copolymer, a linear low-density polyethylene (LLDPE), a metallocene LLDPE (mLLDPE), a modified LLDPE, an LLDPE copolymer, combinations thereof, or any suitable alternative.

In one aspect, the LDPE may be a homopolymer. In another aspect, the LDPE may be a copolymer. In some embodiments, the LDPE copolymer comprises EVA. In some embodiments, the EVA content is about 3% to about 10% by weight of the copolymer. In some embodiments, the EVA content is about 4% to about 8% by weight of the copolymer.

In one aspect, the mLLDPE may be manufactured using a metallocene catalyst. In one aspect, mLLDPE may have short chain branching and minimal long chain branching. In one aspect, an mLLDPE may have a narrower molecular weight distribution when compared to the molecular weight distribution of an LLDPE produced by means other than a metallocene catalyst. In one aspect, an mLLDPE may be a copolymer of ethylene and an alkylene such as propylene, sometimes called propene, butylene, sometimes called butene, pentylene, sometimes called pentene, hexylene, sometimes called hexene, heptylene, sometimes called heptene, or octylene, sometimes called octene. In some embodiments, an mLLDPE may be an ethylene-hexene copolymer. In some embodiments, an mLLDPE may be an ethylene-octene copolymer.

In one aspect, the polypropylene may be a polypropylene copolymer (PP-CoP), an impact polypropylene, a polypropylene impact copolymer, combinations thereof, or any suitable alternative. In some embodiments, the polypropylene may contain an additive. In some examples, a polypropylene impact copolymer is a copolymer of ethylene and propylene. In some examples, a polypropylene impact copolymer is a heterophasic in-situ blend containing an ethylene/propylene rubber component. In some examples, a polypropylene impact copolymer comprises a rubber phase and a polypropylene matrix phase. In some embodiments, a polypropylene impact copolymer may be produced with a Ziegler-Natta catalyst. In some embodiments, a polypropylene impact copolymer is a semi-crystalline thermoplastic resin. In some examples, the polypropylene impact copolymer material contains a nucleating agent.

Process additives, such as slip agents, antiblock agents, or antistatic agents may be added to the formulations to improve the extrusion process and provide additional properties of multi-layer film 10. Colorants in the form of masterbatches may also be added to each formulation. In some embodiments, the multi-layer film is clear and the multi-layer film is substantially free of a colorant.

Multi-layer film 10 may be used on a wrapping machine to form package 18 for holding consumer-care product 24 as shown in FIG. 1. Multi-layer film 10 may form package 18 so that second-seal layer 14 provides an interior surface 20 of package 18 and first-seal layer 12 forms exterior surface 22 arranged to face way from interior surface 20. First and second closures 30, 32 may be formed by heat-sealing multi-layer film 10. Exemplary methods of heat sealing include knife sealing and hot bar sealing.

Multi-layer film 10 includes first-seal layer 12, second-seal layer 14, and deformation-resistant layer 16 as shown in FIGS. 1 and 2. First-seal layer 12 is located in spaced-apart relation to second-seal layer 14. Deformation-resistant layer 16 extends between and interconnects first-seal layer 12 and second-seal layer 14.

In an embodiment, multi-layer film 10 is about 0.5 mils to about 3 mils thick. Multi-layer film 10 may be a particular thickness. The thickness of multi-layer film 10 may be one of the following values: about 0.5 mils, about 0.6 mils, about 0.7 mils, about 0.8 mils, about 0.9 mils, about 1 mil, about 1.1 mils, about 1.2 mils, about 1.3 mils, about 1.4 mils, about 1.5 mils, about 1.55 mils, about 1.6 mils, about 1.61 mils, about 1.62 mils, about 1.7 mils, about 1.75 mils, about 1.8 mils, about 1.9 mils, about 2 mils, about 2.1 mils, about 2.2 mils, about 2.3 mils, about 2.4 mils, about 2.5 mils, about 2.6 mils, about 2.7 mils, about 2.8 mils, about 2.9 mils, or about 3 mils. The thickness of multi-layer film 10 may fall within one of many different ranges. In a first set of ranges, the thickness of multi-layer film 10 is one of the following ranges: about 0.5 mils to about 3 mils, about 0.5 mils to about 2.5 mils, about 0.5 mils to about 2 mils, about 0.5 mils to about 1.8 mils, about 0.5 mils to about 1.6 mils, about 0.5 mils to about 1.5 mils, about 0.5 mils to about 1.2 mils, or about 0.5 mils to about 1 mil. In a second set of ranges, the thickness of multi-layer film 10 is one of the following ranges: about 0.5 mils to about 3 mils, about 0.8 mils to about 3 mils, about 0.9 mils to about 3 mils, about 1 mil to about 3 mils, about 1.4 mils to about 3 mils, about 1.5 mils to about 3 mils, about 1.7 mils to about 3 mils, or about 2 mils to about 3 mils. In a third set of ranges, the thickness of multi-layer film 10 is one of the following ranges: about 0.5 mils to about 3 mils, about 0.7 mils to about 3 mils, about 0.7 mils to about 2 mils, about 0.7 mils to about 1.7 mils, about 0.7 mils to about 1.6 mils, or about 0.8 mils to about 1.6 mils. In an exemplary embodiment, multi-layer film 10 is about 1.5 mils thick. In another exemplary embodiment, multi-layer film 10 is about 1.75 mils thick. In yet another exemplary embodiment, multi-layer film 10 is about 1 mil thick.

In an embodiment, multi-layer film 10 has a density between 0.8 $g/cm^3$ and 1.3 $g/cm^3$. Multi-layer film 10 may be a particular density. The density of multi-layer film 10 may be one of the following values: about 0.8 $g/cm^3$, about 0.85 $g/cm^3$, about 0.9 $g/cm^3$, about 0.91 $g/cm^3$, about 0.92 $g/cm^3$, about 0.93 $g/cm^3$, about 0.94 $g/cm^3$, about 0.95 $g/cm^3$, about 0.96 $g/cm^3$, about 0.97 $g/cm^3$, about 0.98 $g/cm^3$, about 0.99 $g/cm^3$, about 1 $g/cm^3$, about 1.1 $g/cm^3$, about 1.2 $g/cm^3$, or about 1.3 $g/cm^3$. The density of multi-layer film 10 may fall within one of many different ranges. In first set of ranges, the density of multi-layer film 10 is one of the following ranges: about 0.8 $g/cm^3$ to about 1.3 $g/cm^3$, about 0.8 $g/cm^3$ to about 1.2 $g/cm^3$, about 0.8 $g/cm^3$ to about 1.1 $g/cm^3$, about 0.8 $g/cm^3$ to about 1 $g/cm^3$, about 0.8 $g/cm^3$ to about 0.99 $g/cm^3$, or about 0.8 $g/cm^3$ to about 0.98 $g/cm^3$. In a second set of ranges, the density of multi-layer film 10 is one of the following ranges: about 0.8 $g/cm^3$ to about 1.3 $g/cm^3$, about 0.85 $g/cm^3$ to about 1.3 $g/cm^3$, about 0.9 $g/cm^3$ to about 1.3 $g/cm^3$, about 0.93 $g/cm^3$ to about 1.3 $g/cm^3$, about 0.95 $g/cm^3$ to about 1.3 $g/cm^3$, or about 0.96 $g/cm^3$ to about 1.3 $g/cm^3$. In a third a set of ranges, the density of multi-layer film 10 is one of the following ranges: about 0.8 $g/cm^3$ to about 1.3 $g/cm^3$, about 0.9 $g/cm^3$ to about 1.3 g/cm$^3$, about 0.9 g/cm$^3$, to about 1.1 g/cm$^3$, about 0.92 g/cm$^3$ to about 1.1 g/cm$^3$, about 0.93 g/cm$^3$ to about 1.1 g/cm$^3$, about 0.93 g/cm$^3$ to about 1 g/cm$^3$, or about 0.93 g/cm$^3$ to about 0.98 g/cm$^3$.

Each of first-seal layer 12 and second-seal layers 14 may be a particular thickness. The thickness of each of first-seal layer 12 and second-seal layer 14 may be one of the following values: about 0.1 mils, about 0.2 mils, about 0.25 mils, about 0.3 mils, about 0.375 mils, about 0.4 mils, about 0.45 mils, about 0.465 mils, about 0.475 mils, about 0.5 mils, about 0.525 mils, about 0.55 mils, about 0.6 mils, or about 0.7 mils. The thickness of each of first-seal layer 12 and second-seal layer 14 may fall within one of many different ranges. In a set of ranges, the thickness of each of first-seal layer 12 and second-seal layer 14 is one of the following ranges: about 0.1 mils to about 0.6 mils, about 0.2 mils to about 0.6 mils, about 0.2 mils to about 0.5 mils, or about 0.4 mils to about 0.5 mils thick.

In some embodiments, each of first-seal layer 12 and second-seal layer 14 is independently about 10% to about 50% of the total thickness of multi-layer film 10. Each of first-seal layer 12 and second-seal layer 14 may independently be one of several different percentages of the total thickness of multi-layer film 10. The percentage thickness of each of first-seal layer 12 and second-seal layer 14 of multi-layer film 10 may independently be one of the following values: about 10%, about 15%, about 20%, about 25%, about 30%, about 35%, about 40%, about 45%, or about 50% of the total thickness of multi-layer film 10. It is within the present disclosure for the thickness of each of first-seal layer 12 and second-seal layer 14 to independently fall within one of many different ranges. In a set of ranges, the thickness range of each of first-seal layer 12 and second-seal layer 14 is independently one of the following ranges: about 10% to about 50%, about 10% to about 40%, about 15% to about 40%, or about 15% to about 35% of the total thickness multi-layer film 10. In an example, each of first-seal layer 12 and second-seal layer 14 may be about 25% of the total thickness of multi-layer film 10. In another example, each of first-seal layer 12 and second-seal layer 14 may be about 30% of the total thickness of multi-layer film 10. In another example, each of first-seal layer 12 and second-seal layer 14 may be about 20% of the total thickness of multi-layer film 10. In some examples, each of first-seal layer 12 and second-seal layer 14 may be a different percentage thickness of multi-layer film 10 depending on the thickness of multi-layer film 10.

In an embodiment, each composition of first-seal layer 12 and second-seal layer 14 comprises a polyethylene. In some embodiments, the polyethylene is an LLDPE material. In another embodiment, the LLDPE is an LLDPE copolymer. In another embodiment, the LLDPE copolymer is an octene copolymer. In some embodiments, the LLDPE has a melt flow index of about 0.5 g/10 min, about 0.65 g/10 min, or about 1 g/10 min according to ASTM D1238. In some examples, the LLDPE has a density in a range of about 0.91 g/cm$^3$ to about 0.93 g/cm$^3$. In an exemplary embodiment, the LLDPE material is Nova Chemicals® SCLAIR® FP120A. In an exemplary embodiment, the LLDPE is NOVA Chemicals Surpass® FPs016-C Octene sLLDPE.

In another embodiment, the LLDPE may be an mLLDPE. In some examples, the mLLDPE is a copolymer. In some embodiments, the mLLDPE has a melt flow index of about 0.5 g/10 min, about 0.65 g/10 min, or about 1 g/10 min according to ASTM D1238. In some examples, the mLLDPE has a density in a range of about 0.91 g/cm$^3$ to about 0.93 g/cm$^3$. In an exemplary embodiment, the mLLDPE is ExxonMobil™ Exceed™ XP8656. In another exemplary embodiment, the mLLDPE is ExxonMobil™ Exceed™ 8318.

In some embodiments, each composition of first-seal layer 12 and second-seal layer 14 comprises LDPE. In some embodiments, the LDPE may be an LDPE copolymer. In some embodiments, the LDPE copolymer may be an LDPE ethyl vinyl acetate (EVA) copolymer material. In some embodiments, the LDPE material has a melt flow index of about 2 g/10 min according to ASTM D1238. In an exemplary embodiment, the LDPE is ExxonMobil™ LDPE LD 306.57.

In some embodiments, each composition of first-seal layer 12 and second-seal layer 14 independently comprises a blend of an LLDPE and an LDPE. In some embodiments, each composition of first-seal layer 12 and second-seal layer 14 independently comprises a blend of an mLLDPE and an LDPE-EVA copolymer. In some exemplary embodiments, the polyethylenes may be referred to as base resins. In some examples, each composition of first-seal layer 12 and second-seal layer 14 independently comprises a blend of ExxonMobil™ Exceed™ XP8656 and ExxonMobil™ LDPE LD 306.57. In some examples, each composition of first-seal layer 12 and second-seal layer 14 independently comprises a blend of ExxonMobil™ Exceed™ XP8318 and ExxonMobil™ LDPE LD 306.57. In some examples, each composition of first-seal layer 12 and second-seal layer 14 independently comprises a blend of Nova Chemicals® SCLAIR® FP120A and ExxonMobil™ LDPE LD 306.57.

In some embodiments, the mLLDPE material may be up to about 70% by weight of the composition of the seal layers 12, 14. The composition of seal layers 12, 14 may independently comprise one of several different percentages of an LDPE. The percentage by weight amount of the mLLDPE may be selected from the following values: about 25%, about 30%, about 35%, about 40%, about 45%, about 50%, about 52%, about 53%, about 54%, about 55%, about 56%, about 57%, about 58%, about 59%, about 60%, about 61% about 65%, or about 70% by weight of seal layers 12, 14. The amount of the mLLDPE may fall within a series of ranges including about 25% to about 70%, about 30% to about 70%, about 30% to about 65%, about 40% to about 65%, or about 45% to about 65% by weight of seal layers 12, 14.

The composition of seal layers 12, 14 may independently comprise up to about 70% by weight LDPE. The percentage by weight the LDPE may be selected from the following values: about 20%, about 25%, about 30%, about 35%, about 36%, about 37%, about 38%, about 39%, about 40%, about 41%, about 42%, about 45%, about 50%, about 55%, about 60%, about 65%, or about 70% by weight of seal layers 12, 14. The amount of the LDPE may fall within a series of ranges including about 20% to about 70%, about 20% to about 60%, about 25% to about 60%, about 25% to about 50%, or about 30% to about 50% by weight of seal layers 12, 14. These values and ranges apply equally when the LDPE is an LLDPE copolymer. These values and ranges apply equally when the LDPE copolymer comprises EVA.

In some embodiments, each composition of first-seal layer 12 and second-seal layer 14 independently comprises optionally one or more additives such as slip agents, antiblock agents, colorants, or antistatic agents. In some embodiments, each composition of first-seal layer 12 and second-seal layer 14 may independently comprise a slip agent. In some embodiments, each composition of first-seal layer 12 and second-seal layer 14 may independently comprise an antiblock agent. In some embodiments, each of first-seal layer 12 and second-seal layer 14 may independently comprise a colorant. In some embodiments, each of first-seal layer 12 and second-seal layer 14 are substantially free of a colorant. In some embodiments, each of first-seal layer 12 and second-seal layer 14 may independently comprise an antistatic agent. In some embodiments, each composition of first-seal layer 12 and second-seal layer 14 may comprise a slip agent and an antiblock agent. In some embodiments, each composition of first-seal layer 12 and second-seal layer 14 may comprise a slip agent, an antiblock agent, and an antistatic agent.

In certain embodiments, the percentage by weight of the slip agent may fall within a set of ranges including, about 1% to about 10%, about 1% to about 5%, about 1% to about 4%, or about 1% to about 3% by weight of each of first-seal layer 12 and second-seal layer 14. Illustratively, the slip agent may be erucamide. In some embodiments, the slip agent may comprise LDPE. In some embodiments, the slip agent may be Ampacet 10090P.

In certain embodiments, the percentage by weight of the antiblock agent may fall within a set of ranges including, about 1% to about 10%, about 1% to about 5%, about 1% to about 4%, and about 1% to about 3% by weight of each of first-seal layer 12 and second-seal layer 14. In some embodiments, the antiblock agent is Polyfil ABC5000HC.

In certain embodiments, the percentage by weight of the antistatic agent may fall within a set of ranges including, about 1% to about 10%, about 1% to about 5%, about 1% to about 4%, and about 1% to about 3% by weight of each of first-seal layer 12 and second-seal layer 14. In some embodiments, the antistatic agent is Ampacet 104355-N. In some embodiments, the antistatic agent is Ampacet 101140.

Deformation-resistant layer 16 extends between and interconnects first-seal layer 12 with second-seal layer 14. In an embodiment, deformation-resistant layer 16 is about 30% to about 80% of the total thickness multi-layer film 10. Deformation-resistant layer 16 may be one of several different percentages of the thickness of multi-layer film 10. The percentage thickness of deformation-resistant layer 16 of multi-layer film 10 may be one of the following values: about 30%, about 35%, about 40%, about 45%, about 50%, about 55%, about 60%, about 65%, about 70%, about 75%, or about 80% of the total thickness of multi-layer film 10. The percentage thickness of deformation-resistant layer 16 of multi-layer film 10 may fall within one of many different ranges. In a set of ranges, the thickness range of first-seal layer 12 is one of the following ranges: about 30% to about 80%, about 30% to about 70%, about 35% to about 70%, about 35% to about 65%, or about 35% to about 60% of the total thickness of multi-layer film 10. In an embodiment, deformation-resistant layer 16 is about 60% of the total thickness of multi-layer film 10. In some embodiments, deformation-resistant layer 16 is about 50% of the total thickness of multi-layer film 10. In some other embodiments, deformation-resistant layer 16 is about 40% of the total thickness of multi-layer film 10.

Deformation-resistant layer 16 may be a particular thickness. The thickness of deformation-resistant layer 16 may be one of the following values: about 0.3 mils, about 0.4 mils, about 0.5 mils, about 0.6 mils, about 0.62 mils, about 0.7 mils, about 0.75 mils, about 0.8 mils, about 0.9 mils, about 0.93 mils, about 1 mil, about 1.1 mils, about 1.2 mils, about 1.3 mils, about 1.5 mils, about 1.8 mils, or about 2 mils. The thickness of deformation-resistant layer 16 may fall within one of many different ranges. In a set of ranges, the thickness of deformation-resistant layer 16 is one of the following ranges: about 0.3 mils to about 2 mils, about 0.3 mils to about 1.3 mils, about 0.3 mils to about 1.1 mils, about 0.3 mils to about 0.9 mils, about 0.3 mils to about 0.8 mils, or about 0.3 mils to about 0.7 mils thick.

In some embodiments, the composition of deformation-resistant layer 16 comprises a polyethylene material. In some embodiments, the polyethylene material is an LLDPE material. In some embodiments, the LLDPE material is an mLLDPE material. In some examples, the mLLDPE is a copolymer. In some embodiments, the mLLDPE has a melt flow index of about 0.5 g/10 min, about 0.65 g/10 min, or about 1 g/10 min according to ASTM D1238. In some examples, the mLLDPE has a density in a range of about 0.91 g/cm$^3$ to about 0.93 g/cm$^3$. In an exemplary embodiment, the mLLDPE is ExxonMobil™ Exceed™ XP8656. In another exemplary embodiment, the mLLDPE is ExxonMobil™ Exceed™ 8318.

In some embodiments, the polyethylene is an LLDPE material. In another embodiment, the LLDPE is an LLDPE copolymer. In another embodiment, the LLDPE copolymer is an octene copolymer. In some embodiments, the LLDPE has a melt flow index of about 0.5 g/10 min, about 0.65 g/10 min, or about 1 g/10 min according to ASTM D1238. In some examples, the LLDPE has a density in a range of about 0.91 g/cm$^3$ to about 0.93 g/cm$^3$. In an exemplary embodiment, the LLDPE material is Nova Chemicals® SCLAIR® FP120A. In an exemplary embodiment, the LLDPE is NOVA Chemicals Surpass® FPs016-C Octene sLLDPE.

In some embodiments, the composition of deformation-resistant layer 16 comprises an HDPE material. In some embodiments, the HDPE material is DOW® ELITE™ 5960G. In an embodiment, the composition of deformation-resistant layer 16 comprises a HDPE material and an LLDPE material. In some embodiments, the LLDPE material is Nova Chemicals® SCLAIR® FP120A. In another embodiment, the composition of deformation-resistant layer 16 comprises an HDPE material and an mLLDPE material. In some embodiments, the mLLDPE material is ExxonMobil™ Exceed™ XP 8656. In some embodiments, the mLLDPE material is ExxonMobil™ Exceed™ XP 8318.

In some embodiments, the composition of deformation-resistant layer 16 comprises a polypropylene material. In some embodiments, the polypropylene material is a polypropylene homopolymer. In some embodiments, the polypropylene material is a polypropylene copolymer. In some embodiments, the polypropylene material is a polypropylene impact copolymer. In some examples, the polypropylene impact copolymer has a melt flow rate of about 0.45 g/10 min, about 0.5 g/10 min, about 0.75 g/10 min, or a value within a range of about 0.4 g/10 min to about 0.8 g/10 min. In some examples, the polypropylene impact copolymer has a dart impact strength of about 100 g to about 400, about 120 g to about 400 g, or about 300 g to about 400 g as measured by ASTM D-1709. In some examples, the polypropylene impact copolymer is Total Petrochemicals 4170. In some other examples, the polypropylene impact copolymer is LyondellBasell Pro-fax 7823. In some other examples, the polypropylene impact copolymer is Braskem INSPIRE™ 114.

In some embodiments, the composition of deformation-resistant layer 16 comprises a blend of a polypropylene and a polyethylene. In some exemplary embodiments, the polypropylene and the polyethylene materials are described as base resins. In some examples, the polypropylene is a polypropylene impact copolymer. In some embodiments, the polyethylene is an mLLDPE.

The composition of deformation-resistant layer 16 may comprise one of several different percentages of a polypropylene. The percentage by weight amount of a polypropylene may be selected from the following values: about 40%, about 45%, about 50%, about 55%, about 58%, about 59%, about 60%, about 61%, about 62%, about 63%, about 64%, about 65%, about 70%, or about 75% by weight of the composition of deformation-resistant layer 16. The amount of the polypropylene may fall within a series of ranges including about 40% to about 75%, about 45% to about 75%, about 50% to about 75%, about 55% to about 75% and about 55% to about 70% by weight of the composition of deformation-resistant layer 16. These values and ranges apply equally when the polypropylene is a polypropylene copolymer. These values and ranges apply equally when the polypropylene is a polypropylene impact copolymer.

The composition of deformation-resistant layer 16 may comprise one of several different percentages of an LDPE. The percentage by weight amount of a LDPE may be selected from the following values: about 15%, about 17%, about 18%, about 19%, about 20%, about 21%, about 23%, about 24%, about 25%, about 30%, or about 35% by weight of deformation-resistant layer 16. The amount of the LDPE may fall within a series of ranges including about 15% to about 35%, about 15% to about 30%, about 15% to about 25%, about 18% to about 25%, or about 19% to about 25% by weight of deformation-resistant layer 16. These values and ranges apply equally when the LDPE is an LLDPE. These values and ranges apply equally when the LDPE is an LDPE copolymer. These values and ranges apply equally when the LDPE is an mLLDPE.

In an example, a composition of deformation-resistant layer 16 comprises about 62% by weight of a polypropylene impact copolymer and about 23% by weight of an mLLDPE. In another example, a composition of deformation-resistant layer 16 comprises about 60% by weight of a polypropylene impact copolymer and about 23% by weight of an mLLDPE.

In some embodiments, a composition of deformation-resistant layer 16 may optionally comprise one or more additives such as slip agents, antiblock agents, colorants, or antistatic agents. In some embodiments, deformation-resistant layer 16 comprises a slip agent. In some embodiments, a composition of deformation-resistant layer 16 comprises an antiblock agent. In some embodiments, a composition of deformation-resistant layer 16 comprises a colorant. In some embodiments, a composition of deformation-resistant layer 16 comprises an antistatic agent. In some embodiments, a composition of deformation-resistant layer 16 comprises a slip agent and a colorant. In some embodiments, a composition of deformation-resistant layer 16 comprises a slip agent, a colorant, and an antistatic agent. In some embodiments, deformation-resistant layer 16 is substantially free of a colorant.

In certain embodiments, the percentage by weight of the slip agent may fall within a set of ranges including, about 1% to about 10%, about 1% to about 5%, about 1% to about 4%, or about 1% to about 3% by weight of a composition of deformation-resistant layer 16. Illustratively, the slip agent may be erucamide. In some embodiments, the slip agent comprises LDPE. In some embodiments, the slip agent is Ampacet 10090P.

In some embodiments, the percentage by weight of the colorant may fall within a set of ranges including, about 3% to about 25%, about 5% to about 25%, about 10% to about 25%, or about 10% to about 20% by weight of a composition of deformation-resistant layer 16. Illustratively, the colorant may be in the form of a masterbatch. In some embodiments, the colorant comprises polyethylene. In some embodiments, the colorant is Ampacet 111017P.

In certain embodiments, the percentage by weight of the antistatic agent may fall within a set of ranges including, about 1% to about 10%, about 1% to about 5%, about 1% to about 4%, or about 1% to about 3% by weight of a composition of deformation-resistant layer 16. In some embodiments, the antistatic agent is Ampacet 104355-N. In some embodiments, the antistatic agent is Ampacet 101140.

Multi-layer film 10 may be used to form package 18 to store a consumer-care product 24. Package 18 includes bag 28 formed to include interior product-storage region 26, first closure 30 located at a first end 31 of bag 28, and second closure 32 located on an opposite second end 33 of bag 28 in spaced-apart relation to first closure 30. Bag 28 may be formed by wrapping multi-layer film 10 around consumer-care product 24. After wrapping consumer-care product 24, first and second closures 30, 32 may be formed by heat sealing. Multi-layer film 10 may be used to store consumer-care product 24 to minimize the deformation of exterior surface 22 of package 18 during handling of package 18. Multi-layer film 10 may also provide superior heat seal strength to first and second closures 30, 32 to retain consumer-care product 24 in package 18.

A method of making package 18 may include the step of heat sealing first end 31 to form first closure 30. The method may further include inserting a consumer-care product 24 into interior-product storage region 26. The method may further include heat sealing second end 33 to form second closure 32. In some embodiments, the step of inserting consumer-care product 24 occurs before a step of heat sealing. In some embodiments, the step of inserting consumer-care product 24 occurs after first closure 30 is formed. Illustratively, the method of making package 18 with multi-layer film 10 may lead to improved bagging rates and lower equipment costs. These improvements may be due in part to higher heat sealing temperatures and reduced dwell times. Illustratively the package 18 formed with multi-layer film 10 may have a smoother and cleaner appearance.

The step of heat sealing multi-layer film 10 may be performed at a wide range of temperatures. The step of heat sealing may be performed at about 190° F., about 200° F., about 210° F., about 220° F., about 230° F., about 240° F., about 250° F., about 260° F., about 270° F., about 280° F., about 290° F., about 300° F., about 310° F., about 320° F., about 330° F., about 340° F., about 350° F., or about 360° F. The step of heat sealing may be performed at a temperature within a first set of ranges of about 190° F. to about 360° F., about 190° F. to about 340° F., about 190° F. to about 330° F., about 190° F. to about 300° F., about 190° F. to about 280° F., about 190° F. to about 260° F., or about 190° F. to about 240° F. The step of heat sealing may be performed at a temperature within a second set of ranges of about 190° F. to about 360° F., about 210° F. to about 360° F., about 230° F. to about 360° F., about 250° F. to about 360° F., about 270° F. to about 360° F., about 280° F. to about 360° F., about 300° F. to about 360° F., about 320° F. to about 360° C., or about 340° C. to about 360° C. Illustratively, first and second closures 30, 32 do not fail from burn through at the temperatures described herein. Illustratively, first and second closures 30, 32 do not fail from peeling.

The heat seal formed in multi-layer film 10 may have a particular strength. The strength of the heat seal or the first or second closure 30, 32 may be at least 10 g, at least 50 g, at least 100 g, at least 200 g, at least 300 g, at least 400 g, at least 500 g, at least 600 g, or at least 700 g. The strength of the heat seal or the first or second closure 30, 32 may be about 10 g, about 50 g, about 100 g, about 150 g, about 200 g, about 250 g, about 300 g, about 350 g, about 400 g, about 450 g, about 500 g, about 550 g, about 600 g, about 650 g, about 700 g, about 750 g, about 800 g, about 850 g, about 900 g, about 950 g, about 1000 g, about 1050 g, about 1100 g, about 1150 g, about 1200 g, about 1250 g, about 1300 g, about 1350 g, about 1400 g, about 1450 g, about 1500 g, about 1550 g, about 1600 g, about 1650 g, or about 1700 g. The strength of the heat seal for first or second closure 30, 32 be within a range of about 10 g to about 1700 g, about 100 g to about 1700 g, about 200 g to about 1700 g, about 300 g to about 1700 g, about 400 g to about 1700 g, about 500 g to about 1700 g, about 600 g to about 1700 g, about 650 g to about 1700 g, about 700 g to about 1700 g, about 750 g to about 1700 g, about 800 g to about 1700 g, about 850 g to about 1700 g, about 900 g to about 1700 g, or about 1000 g to about 1700 g. Illustratively, the strength of the heat seal may be such that first and second closures 30, 32 fail at a location other than the heat seal.

Illustratively, multi-layer films 10 described herein may be heat sealed over a wide range of temperatures, sometimes called a heat-seal window. Illustratively, the heat seal window is a range of temperatures within which multi-layer film 10 can be heat-sealed and provide a sufficient heat seal. In a first set of ranges, the heat seal window can be about 210° F. to about 400° F., about 230° F. to about 400° F., about 250° F. to about 400° F., about 270° F. to about 400° F., about 290° F. to about 400° F., about 300° F. to about 400° F., about 310° F. to about 400° F., about 320° F. to about 400° F., or about 340° F. to about 400° F. In a second set of ranges, the heat seal window can be about 210° F. to about 350° F., about 230° F. to about 350° F., about 250° F. to about 350° F., about 270° F. to about 350° F., about 290° F. to about 350° F., about 300° F. to about 350° F., about 310° F. to about 350° F., about 320° F. to about 350° F., or about 340° F. to about 350° F.

Illustratively, the heat-seal window may span at least 50° F., at least 60° F., at least 70° F., at least 80° F., at least 90° F., at least 100° F., at least 110° F., at least 120° F., at least 130° F., or at least 140° F.

In certain aspects of the present disclosure, the heat seal is formed during a particular dwell time. In some embodiments, the dwell time may be selected from a range of about 5 ms to about 1500 ms, about 5 ms to about 1000 ms, about 5 ms to about 500 ms, about 5 ms to about 100 ms, about 5 ms to about 50 ms, or about 5 ms to about 25 ms.

In some examples in accordance with the present disclosure, multi-layer film 10 may be a 3-layer film. In some other examples, a multi-layer film may be a 5-layer film. In some examples, a multi-layer film may be a 7-layer film. In some examples, a multi-layer film including deformation-resistant layer 16 may comprise any suitable number of layers.

In certain aspects of the present disclosure, multi-layer films 10 including deformation-resistant layers 16 comprising a polypropylene impact copolymer exhibit improved properties compared to multi-layer films 10 including deformation-resistant layers 16 comprising HDPE. The improved properties may be related to tensile strengths, puncture resistance, tear resistance, heat-seal windows, and heat-seal strengths. In certain aspects of the present disclosure, multi-layer films 10 including deformation-resistant layers 16 comprising a polypropylene impact copolymer may be thinner and have improved properties when compared to thicker multi-layer films 10 including deformation-resistant layers 16 comprising HDPE. For example, multi-layer film 10 of Examples 17 and 18 has comparable or improved properties, such as tensile strengths and dart drop performance, in comparison to multi-layer film 10 of Examples 1-4. In certain aspects of the present disclosure, multi-layer films 10 including deformation-resistant layers 16 comprising a polypropylene impact copolymer may provide an increased heat-seal temperature window when compared to multi-layer films 10 including deformation-resistant layers 16 comprising HDPE.

In an embodiment, multi-layer film 10 may have a dart drop (26") performance of about 100 g to about 400 g as measured by ASTM D1709. Multi-layer film 10 may have a particular dart drop (26") performance. The dart drop (26") performance of multi-layer film 10 as measured by ASTM D1709 may be one of the following values: about 100 g, about 110 g, about 120 g, about 130 g, about 140 g, about 150 g, about 160 g, about 170 g, about 174 g, about 180 g, about 187 g, about 190 g, about 200 g, about 210 g, about 220 g, about 230 g, about 240 g, about 241 g, about 250 g, about 260 g, about 266 g, about 270 g, about 279 g, about 280 g, about 290 g, about 300 g, about 310 g, about 320 g, about 330 g, about 340 g, about 350 g, about 360 g, about 370 g, about 380 g, about 390 g, or about 400 g. The dart drop (26") performance of multi-layer film 10 may fall within one of many different ranges. In a set of ranges, the dart drop (26") performance as measured by ASTM D1709 is one of the following ranges: about 100 g to about 400 g, about 120 g to about 400 g, about 150 g to about 400 g, about 200 g to about 400 g, about 200 g to about 350 g, about 200 g to about 320 g, or about 250 g to about 320 g.

In an embodiment, multi-layer film 10 may have a slow puncture (¼") as measured by ASTM F1306 of about 800 gf to about 3000 gf or any suitable value therebetween. Multi-layer film 10 may have a particular slow puncture (¼") performance. The slow puncture (¼") performance of multi-layer film 10 as measured by ASTM F1306 may be one of the following values: about 800 gf, about 874 gf, about 900 gf, about 1000 gf, about 1100 gf, about 1162 gf, about 1200 gf, about 1300 gf, about 1400 gf, about 1500 gf, about 1512 gf, about 1600 gf, about 1700 gf, about 1728 gf, about 1738 gf, about 1743 gf, about 1771 gf, about 1800 gf, about 1854 gf, about 1900 gf, about 2000 gf, about 2100 gf, about 2200 gf, about 2300 gf, about 2400 gf, about 2500 gf, about 2600 gf, about 2700 gf, about 2800 gf, about 2900 gf, or about 3000 gf. The slow puncture (¼") of multi-layer film 10 may fall within one of many different ranges. In a set of ranges, the da slow puncture (¼") performance of multi-layer film 10 as measured by ASTM F1306 is one of the following ranges: about 800 gf to about 3000 gf, about 800 gf to about 2500 gf, about 1200 gf to about 2500 gf, about 1300 gf to about 2500 gf, about 1500 gf to about 2500 gf, about 1500 gf to about 2200 gf, or about 1500 gf to about 2000 gf.

Multi-layer films 10 in accordance with the present disclosure may have various characteristics including layering, color, gauge, basis weight, light transmission, coefficient of friction (COF) kinetic in/in, COF kinetic out/out, stress at peak in the machine direction (MD), strain at peak in the MD, stress at 5% strain MD, stress at 10% strain MD, stress at 25% strain MD, secant modulus MD (1%), Elmendorf tear MD arm, Elmendorf tear MD, stress at peak in the transverse direction (TD), strain at peak in the TD, stress at 5% strain TD, stress at 10% strain TD, stress at 25% strain TD, secant modulus (1%) TD, Elmendorf tear TD arm, Elmendorf tear TD, dart drop (26"), and slow puncture (1.4").

In one example, the gauge may be about 0.9 mils to about 1.8 mils or any suitable value therebetween. In another example, the gauge may be about 0.97 mils to about 1.75 mils or any suitable value therebetween.

In one example, the basis weight may be about 23 $g/m^2$, to about 48 $g/m^2$ or any suitable value therebetween. In another example, the basis weight may be about 24.1 g/m$^2$, to about 46.4 g/m$^2$ or any suitable value therebetween.

In one example, light transmission may be about 35% to about 65% or any suitable value therebetween. In another example, light transmission may be about 41.77% to about 60.40% or any suitable value therebetween.

In one example, COF kinetic in/in may be about 0.1 to about 0.2 or any suitable value therebetween. In another example, COF kinetic in/in may be about 0.13 to about 0.16 or any suitable value therebetween.

In one example, COF kinetic out/out may be about 0.1 to about 0.5 or any suitable value therebetween. In another example, COF kinetic out/out may be about 0.14 to about 0.44 or any suitable value therebetween.

In one example, stress at the peak in the MD may be about 4000 PSI to about 7200 PSI or any suitable value therebetween. In another example, stress at the peak in the MD may be about 4039 PSI to about 7052 PSI or any suitable value therebetween.

In one example, strain at the peak in the MD may be about 400% to about 650% or any suitable value therebetween. In another example, strain at the peak in the MD may be about 411% to about 612% or any suitable value therebetween.

In one example, stress at 5% strain MD is about 1200 PSI to about 2300 PSI or any suitable value therebetween. In another example, stress at 5% strain MD is about 1287 PSI to about 2220 PSI or any suitable value therebetween.

In one example, the stress at 10% strain MD is about 1600 PSI to about 2700 PSI or any suitable value therebetween. In another example, stress at 10% strain MD is about 1609 PSI to about 2623 PSI or any suitable value therebetween.

In one example, stress at 25% strain MD is about 1600 PSI to about 2800 PSI or any suitable value therebetween. In another example, stress at 25% strain MD is about 1696 PSI to about 2765 PSI or any suitable value therebetween.

In one example secant modulus MD (1%) is about 34000 PSI to about 80000 PSI or any suitable value therebetween. In another example, secant modulus MD (1%) is about 34434 PSI to about 79233 PSI or any suitable value therebetween.

In one example, the Elmendorf tear MD arm is about 150 g to about 450 g or any suitable value therebetween. In another example, the Elmendorf tear MD arm is about 200 g to about 400 g or any suitable value therebetween.

In one example, Elmendorf tear MD is about 38 gf to about 275 gf or any suitable value therebetween. In another example, Elmendorf tear MD is about 40.72 gf to about 271.2 gf or any suitable value therebetween.

In one example, the stress at the peak in the TD is about 3500 PSI to about 5600 PSI or any suitable value therebetween. In another example, the stress at the peak in the TD is about 3642 PSI to about 5563 PSI or any suitable value therebetween.

In one example, the strain at the peak in the TD is about 600% to about 850% or any suitable value therebetween. In another example, the strain at the peak in the TD is about 686% to about 792% or any suitable value therebetween.

In one example, stress at 5% strain TD is about 1300 PSI to about 2100 PSI or any suitable value therebetween. In another example, stress at 5% strain TD is about 1373 PSI to about 2051 PSI or any suitable value therebetween.

In one example, stress at 10% strain TD is about 1600 PSI to about 2400 PSI or any suitable value therebetween. In another example, stress at 10% strain TD is about 1698 PSI to about 2322 PSI or any suitable value therebetween.

In one example, stress at 25% strain TD is about 1500 PSI to about 2200 PSI or any suitable value therebetween. In another example, stress at 25% strain TD is about 1587 PSI to about 2078 PSI or any suitable value therebetween.

In one example, secant modulus (1%) TD is about 40000 PSI to about 77000 PSI or any suitable value therebetween. In another example, secant modulus (1%) TD is about 40050 PSI to about 76103 PSI or any suitable value therebetween.

In one example, the Elmendorf tear TD arm is about 1400 g to about 1700 g. In another example, the Elmendorf tear TD arm is about 1600 g.

In one example, Elmendorf tear TD is about 600 gf to about 1200 gf or any suitable value therebetween. In another example, Elmendorf tear TD is about 617.28 gf to about 1195.52 gf or any suitable value therebetween.

In one example, dart drop (26") is about 100 g to about 400 g or any suitable value therebetween. In another example, dart drop (26") is about 120 g to about 279 g or any suitable value therebetween.

In one example, slow puncture (¼") is about 800 gf to about 3000 gf or any suitable value therebetween. In another example, slow puncture (¼") is about 874 gf to about 1854 gf or any suitable value therebetween.

A package comprises a bag formed to include an interior product storage region, and a first closure located on a first end of the bag. The bag is formed of a multi-layer film including a first-seal layer, a second-seal layer, and a deformation-resistant layer extending between and interconnecting the first-seal layer and the second-seal layer. The multi-layer film is configured to provide means for minimizing deformation of the bag during handling and maximizing a heat-seal temperature range so that an outer surface of the package remains uninterrupted.

A multi-layer film comprises a first-seal layer, a second-seal layer located in spaced-apart relation to the first-seal layer, and a deformation-resistant layer arranged to extend between and interconnect the first-seal layer and the second-seal layer. The deformation-resistant layer is configured to provide means for minimizing deformation of the multi-layer film during handling so that an outer surface of the multi-layer film remains uninterrupted.

In some embodiments, a multi-layer film consists of a first-seal layer, a second-seal layer located in spaced-apart relation to the first-seal layer, and a deformation-resistant layer arranged to extend between and interconnect the first-seal layer and the second-seal layer.

The deformation-resistant layer includes, for example, a polypropylene impact copolymer material and a metallocene LLDPE (mLLDPE) material. The polypropylene impact copolymer may be up to about 90% by weight of the deformation-resistant layer. The polypropylene impact copolymer may be about 45% by weight to about 75% by weight of the deformation-resistant layer. The metallocene LLDPE (mLLDPE) material may be up to about 60% by weight of the deformation-resistant layer. The mLLDPE material may be about 10% by weight to about 40% by weight of the deformation-resistant layer.

EXAMPLES

The following examples are set forth for purposes of illustration only. Parts and percentages appearing in such examples are by weight unless otherwise stipulated. All ASTM, ISO, and other standard test methods cited or referred to in this disclosure are incorporated by reference in their entirety.

Example 1

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 1 to correlate the layer composition with the layer thickness. The instant example is provided to evaluate the properties of the exemplary multi-layer film.

Each of a first- and a second-seal layer (1.1, 1.3) comprises Nova Chemicals® SCLAIR® FP120A and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58.0% | Nova Chemicals ® SCLAIR ® FP120A |
| 38.5% | ExxonMobil ™ LDPE LD 306.57 |
| 1.5% | Ampacet 10090P |
| 2.0% | Polyfil ABC5000HC |

The resins, the slip agent, and the antiblock were added to an extruder hopper and combined via blending to provide a formulation. The formulation was then heated in the extruder to form a molten material.

A deformation-resistant layer (1.2) comprises DOW® ELITE™ 5960G and Nova Chemicals® SCLAIR® FP120A as the base resins Ampacet 10090P was added as a slip agent and Ampacet 111017P masterbatch was added. The percentages by weight of the components were about:

| | |
|---|---|
| 32% | DOW ® ELITE ™ 5960G |
| 50.5% | Nova Chemicals ® SCLAIR ® FP120A |
| 1.5% | Ampacet 10090P |
| 16% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 1 with a gauge of 1.5 mils, a density of 0.983 g/cm$^3$, and with layer thicknesses as described in Table 1.

TABLE 1

Target Layer Thicknesses

| Layer | Thickness (%) | Thickness (mil) |
|---|---|---|
| 1.1 | 25 | 0.375 |
| 1.2 | 50 | 0.750 |
| 1.3 | 25 | 0.375 |

Example 2

Multi-Layer Film Properties

The formulation and process of a multi-layer film in accordance with Example 1 was evaluated. The co-extruded film as described in Example 1 was found to have the properties described in Table 2. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 2

Multi-layer film characteristics

| Physical Properties Description | Units | Film 1 Control |
|---|---|---|
| Layering | | 25/50/25 |
| Color | | White |
| Gauge | mil | 1.50 |
| Basis Weight | g/m$^2$ | 46.4 |
| Light Transmission | % | — |
| COF, Kinetic - In\In | — | 0.159 |
| COF, Kinetic - Out\Out | — | 0.247 |
| Stress @ Peak MD | PSI | 4601 |
| Strain @ Peak MD | % | 612 |
| Stress @ 5% Strain MD | PSI | 1287 |
| Stress @ 10% Strain MD | PSI | 1609 |
| Stress @ 25% Strain MD | PSI | 1696 |
| Secant Modulus MD (1%) | PSI | 34434 |
| Elmendorf Tear MD Arm | g | 400 |
| Elmendorf Tear MD | gf | 271.2 |
| Stress @ Peak TD | PSI | 4209 |
| Strain @ Peak TD | % | 787 |
| Stress @ 5% Strain TD | PSI | 1373 |
| Stress @ 10% Strain TD | PSI | 1709 |
| Stress @ 25% Strain TD | PSI | 1632 |
| Secant Modulus TD (1%) | PSI | 40050 |
| Elmendorf Tear TD Arm | g | 1600 |
| Elmendorf Tear TD | gf | 1195.5 |
| Dart Drop (26") | g | 139 |
| Slow Puncture - ¼" (D3) | gf | 1728 |

Example 3

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 3 to correlate the layer composition with the layer thickness. The instant example is provided to evaluate the properties of the exemplary multi-layer film.

Each of a first- and a second-seal layer (2.1, 2.3) comprises Nova Chemicals® SCLAIR® FP120A and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58.0% | Nova Chemicals ® SCLAIR ® FP120A |
| 38.5% | ExxonMobil ™ LDPE LD 306.57 |
| 1.5% | Ampacet 10090P |
| 2.0% | Polyfil ABC5000HC |

The resins, the slip agent, and the antiblock were added to an extruder hopper and combined via blending to provide a formulation. The formulation was then heated in the extruder to form a molten material.

A deformation-resistant layer (2.2) comprises DOW® ELITE™ 5960G and Nova Chemicals® SCLAIR® FP120A as the base resins Ampacet 10090P was added as a slip agent and Ampacet 111017P masterbatch was added. The percentages by weight of the components were about:

| | |
|---|---|
| 63.5% | DOW ® ELITE ™ 5960G |
| 19.0% | Nova Chemicals ® SCLAIR ® FP120A |
| 1.5% | Ampacet 10090P |
| 16% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 2 with a gauge of 1.5 mils, a density of 0.983 g/cm$^3$, and with layer thicknesses as described in Table 3.

TABLE 3

| Target Layer Thicknesses | | |
|---|---|---|
| Layer | Thickness (%) | Thickness (mil) |
| 2.1 | 25 | 0.375 |
| 2.2 | 50 | 0.750 |
| 2.3 | 25 | 0.375 |

Example 4

Multi-Layer Film Properties

The formulation and process of a multi-layer film in accordance with Example 3 was evaluated. The co-extruded film as described in Example 3 was found to have the properties described in Table 4 Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 4

| Multi-layer film characteristics | | |
|---|---|---|
| Physical Properties Description | Units | Film 2 Control + 2X HD |
| Layering | | 25/50/25 |
| Color | | White |
| Gauge | mil | 1.570 |
| Basis Weight | g/m$^2$ | 37.5 |
| Light Transmission | % | 48.0 |
| COF, Kinetic - In\In | — | 0.159 |
| COF, Kinetic - Out\Out | — | 0.155 |
| Stress @ Peak MD | PSI | 4039 |
| Strain @ Peak MD | % | 609 |
| Stress @ 5% Strain MD | PSI | 1719 |
| Stress @ 10% Strain MD | PSI | 2016 |
| Stress @ 25% Strain MD | PSI | 2025 |
| Secant Modulus MD (1%) | PSI | 53526 |
| Elmendorf Tear MD Arm | g | 200 |
| Elmendorf Tear MD | gf | 83.7 |
| Stress @ Peak TD | PSI | 3642 |
| Strain @ Peak TD | % | 781 |
| Stress @ 5% Strain TD | PSI | 2014 |
| Stress @ 10% Strain TD | PSI | 2274 |
| Stress @ 25% Strain TD | PSI | 2018 |
| Secant Modulus TD (1%) | PSI | 66146 |
| Elmendorf Tear TD Arm | g | 1600 |
| Elmendorf Tear TD | gf | 1080.6 |
| Dart Drop (26") | g | 120 |
| Slow Puncture - 1/4" (D3) | gf | 1512 |

Example 5

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 5 to correlate the layer composition with the layer thickness. The instant example is provided to evaluate the properties of the exemplary multi-layer film.

A first- and second-seal layer (3.1, 3.3) comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (3.2) comprises DOW® ELITE™ 5960G and ExxonMobil™ Exceed™ XP8656 as the base resins Ampacet 10090P was added as a slip agent and Ampacet 111017P masterbatch was added. The percentages by weight of the components were about:

| | |
|---|---|
| 60% | DOW ® ELITE ™ 5960G |
| 23% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form a multi-layer film with a gauge of 1.5 mils, a density of 0.977 g/cm$^3$, and with layer thicknesses as described in Table 5.

TABLE 5

| Target Layer Thicknesses | | |
|---|---|---|
| Layer | Thickness (%) | Thickness (mil) |
| 3.1 | 20 | 0.30 |
| 3.2 | 60 | 0.93 |
| 3.3 | 20 | 0.30 |

Example 6

Multi-Layer Film Properties

The formulation and process of a multi-layer film in accordance with Example 5 was evaluated. The co-extruded film as described in Example 5 was found to have the properties described in Table 6. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 6

| Multi-layer film characteristics | | |
|---|---|---|
| Physical Properties Description | Units | Film 3 |
| Layering | | 20/60/20 |
| Color | | White |
| Gauge | mil | 1.488 |
| Basis Weight | g/m$^2$ | 38.4 |
| Light Transmission | % | 44.4 |
| COF, Kinetic-In\In | — | 0.125 |
| COF, Kinetic-Out\Out | — | 0.163 |
| Stress @ Peak MD | PSI | 4545 |
| Strain @ Peak MD | % | 535 |
| Stress @ 5% Strain MD | PSI | 1705 |
| Stress @ 10% Strain MD | PSI | 2013 |
| Stress @ 25% Strain MD | PSI | 2043 |
| Secant Modulus MD (1%) | PSI | 52254 |
| Elmendorf Tear MD Arm | g | 200 |
| Elmendorf Tear MD | gf | 154.6 |
| Stress @ Peak TD | PSI | 3895 |
| Strain @ Peak TD | % | 695 |
| Stress @ 5% Strain TD | PSI | 1847 |
| Stress @ 10% Strain TD | PSI | 2110 |

TABLE 6-continued

| Multi-layer film characteristics | | |
|---|---|---|
| Physical Properties Description | Units | Film 3 |
| Stress @ 25% Strain TD | PSI | 1905 |
| Secant Modulus TD (1%) | PSI | 62305 |
| Elmendorf Tear TD Arm | g | 3200 |
| Elmendorf Tear TD | gf | 1405.8 |
| Dart Drop (26") | g | 196 |
| Slow Puncture-¼" (D3) | gf | 1534 |

Example 7

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 7 to correlate the layer composition with the layer thickness. The instant example is provided to evaluate the properties of the exemplary multi-layer film.

Each of a first- and a second-seal layer (4.1, 4.3) comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (4.2) comprises Total Petrochemicals 4170 and ExxonMobil™ Exceed™ XP8656 Ampacet 10090P was added as a slip agent and Ampacet 111017P masterbatch was added. The percentages by weight of the components were about:

| | |
|---|---|
| 60% | Total Petrochemicals 4170 |
| 23% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 4 with a gauge of 1.55 mils, a density of 0.949 g/cm$^3$, and with layer thicknesses as described in Table 7.

TABLE 7

| Target Layer Thicknesses | | |
|---|---|---|
| Layer | Thickness (%) | Thickness (mil) |
| 4.1 | 30 | 0.465 |
| 4.2 | 40 | 0.620 |
| 4.3 | 30 | 0.465 |

Example 8

Multi-Layer Film Properties

The formulation and process of a multi-layer film in accordance with Example 7 was evaluated. The co-extruded film as described in Example 7 was found to have the properties described in Table 8. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 8

| Multi-layer film characteristics | | |
|---|---|---|
| Physical Properties | Units | Film 4 |
| Layering | | 30/40/30 |
| Color | | White |
| Gauge | mil | 1.550 |
| Basis Weight | g/m$^2$ | 38.4 |
| Light Transmission | % | 50.7 |
| COF, Kinetic-In\In | — | 0.144 |
| COF, Kinetic-Out\Out | — | 0.242 |
| Stress @ Peak MD | PSI | 6753 |
| Strain @ Peak MD | % | 486 |
| Stress @ 5% Strain MD | PSI | 1521 |
| Stress @ 10% Strain MD | PSI | 1938 |
| Stress @ 25% Strain MD | PSI | 2297 |
| Secant Modulus MD (1%) | PSI | 50824 |
| Elmendorf Tear MD Arm | g | 200 |
| Elmendorf Tear MD | gf | 72.2 |
| Stress @ Peak TD | PSI | 5193 |
| Strain @ Peak TD | % | 729 |
| Stress @ 5% Strain TD | PSI | 1544 |
| Stress @ 10% Strain TD | PSI | 1784 |
| Stress @ 25% Strain TD | PSI | 1724 |
| Secant Modulus TD (1%) | PSI | 53290 |
| Elmendorf Tear TD Arm | g | 1600 |
| Elmendorf Tear TD | gf | 1190.0 |
| Dart Drop (26") | g | 279 |
| Slow Puncture-¼" (D3) | gf | 1162 |

Example 9

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 9 to correlate the layer composition with the layer thickness. The instant example is provided to evaluate the properties of the exemplary multi-layer film.

A first- and a second-seal layer (5.1, 5.3) each comprise ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (5.2) comprises Total 4170 and ExxonMobil™ Exceed™ XP8656. Ampacet 10090P was added as a slip agent and Ampacet 111017P masterbatch was added. The percentages by weight of the components were about:

| | |
|---|---|
| 60% | Total Petrochemicals 4170 |
| 23% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form a multi-layer film with a gauge of 1.5 mils, a density of 0.961 g/cm$^3$, and with layer thicknesses as described in Table 9.

TABLE 9

| Target Layer Thicknesses | | |
|---|---|---|
| Layer | Thickness (%) | Thickness (mil) |
| 5.1 | 20 | 0.30 |
| 5.2 | 60 | 0.93 |
| 5.3 | 20 | 0.30 |

Example 10

Multi-Layer Film Properties

The formulation and process of a multi-layer film in accordance with Example 9 was evaluated. The co-extruded film as described in Example 9 was found to have the properties described in Table 10. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 10

| Multi-layer film characteristics | | |
|---|---|---|
| Physical Properties | Units | Film 5 |
| Layering | | 20/60/20 |
| Color | | White |
| Gauge | mil | 1.500 |
| Basis Weight | g/m$^2$ | 36.1 |
| Light Transmission | % | 41.8 |
| COF, Kinetic-In\In | — | 0.141 |
| COF, Kinetic-Out\Out | — | 0.142 |
| Stress @ Peak MD | PSI | 6949 |
| Strain @ Peak MD | % | 504 |
| Stress @ 5% Strain MD | PSI | 1821 |
| Stress @ 10% Strain MD | PSI | 2242 |
| Stress @ 25% Strain MD | PSI | 2590 |
| Secant Modulus MD (1%) | PSI | 61081 |
| Elmendorf Tear MD Arm | g | 200 |
| Elmendorf Tear MD | gf | 54.8 |
| Stress @ Peak TD | PSI | 5563 |
| Strain @ Peak TD | % | 736 |
| Stress @ 5% Strain TD | PSI | 1738 |
| Stress @ 10% Strain TD | PSI | 1957 |
| Stress @ 25% Strain TD | PSI | 1736 |
| Secant Modulus TD (1%) | PSI | 63519 |
| Elmendorf Tear TD Arm | g | 1600 |
| Elmendorf Tear TD | gf | 764.2 |
| Dart Drop (26") | g | 266 |
| Slow Puncture-¼" (D3) | gf | 1771 |

Example 11

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 11 of the present disclosure to correlate the layer composition with the layer thickness. The instant example is provided to evaluate the properties of the exemplary multi-layer film.

A first- and a second-seal layer (6.1, 6.3) each comprise Nova Chemicals® SCLAIR® FP120A and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58% | Nova Chemicals ® SCLAIR ® FP120A |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (6.2) comprises Total 4170 and ExxonMobil™ Exceed™ XP8656. Ampacet 10090P was added as a slip agent and Ampacet 111017P masterbatch was added. The percentages by weight of the components were about:

| | |
|---|---|
| 60% | Total Petrochemicals 4170 |
| 23% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form a multi-layer film with a gauge of 1.5 mils, a density of 0.963 g/cm$^3$, and with layer thicknesses as described in Table 11.

TABLE 11

| Target Layer Thicknesses | | |
|---|---|---|
| Layer | Thickness (%) | Thickness (mil) |
| 6.1 | 20 | 0.30 |
| 6.2 | 60 | 0.93 |
| 6.3 | 20 | 0.30 |

Example 12

Multi-Layer Film Properties

The formulation and process of a multi-layer film in accordance with Example 11 was evaluated. The co-extruded film as described in Example 11 was found to have the properties described in Table 12. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 12

| Multi-layer film characteristics | | |
|---|---|---|
| Physical Properties | Units | Film 6 |
| Layering | | 20/60/20 |
| Color | | White |
| Gauge | mil | 1.500 |

TABLE 12-continued

| Multi-layer film characteristics | | |
|---|---|---|
| Physical Properties | Units | Film 6 |
| Basis Weight | g/m$^2$ | 36.1 |
| Light Transmission | % | 41.8 |
| COF, Kinetic-In\In | — | 0.141 |
| COF, Kinetic-Out\Out | — | 0.142 |
| Stress @ Peak MD | PSI | 6949 |
| Strain @ Peak MD | % | 504 |
| Stress @ 5% Strain MD | PSI | 1821 |
| Stress @ 10% Strain MD | PSI | 2242 |
| Stress @ 25% Strain MD | PSI | 2590 |
| Secant Modulus MD (1%) | PSI | 61081 |
| Elmendorf Tear MD Arm | g | 200 |
| Elmendorf Tear MD | gf | 54.8 |
| Stress @ Peak TD | PSI | 5563 |
| Strain @ Peak TD | % | 736 |
| Stress @ 5% Strain TD | PSI | 1738 |
| Stress @ 10% Strain TD | PSI | 1957 |
| Stress @ 25% Strain TD | PSI | 1736 |
| Secant Modulus TD (1%) | PSI | 63519 |
| Elmendorf Tear TD Arm | g | 1600 |
| Elmendorf Tear TD | gf | 764.2 |
| Dart Drop (26") | g | 266 |
| Slow Puncture-¼" (D3) | gf | 1771 |

Example 13

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 13 to correlate the layer composition with the layer thickness. The instant example is provided to evaluate the properties of the exemplary multi-layer film.

A first- and a second-seal layer (7.1, 7.3) each comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (7.2) comprises LyondellBasell Pro-fax 7823 and ExxonMobil™ Exceed™ XP8656. Ampacet 10090P was added as a slip agent and Ampacet 111017P masterbatch was added. The percentages by weight of the components were about:

| | |
|---|---|
| 60% | LyondellBasell Pro-fax 7823 |
| 23% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The resin was added to an extruder hopper. The resin was then heated in the extruder to form a molten material.

The molten materials described above were co-extruded and blown to form a multi-layer film with a gauge of 1.5 mils, a density of 0.961 g/cm$^3$, and with layer thicknesses as described in Table 13.

TABLE 13

| Target Layer Thicknesses | | |
|---|---|---|
| Layer | Thickness (%) | Thickness (mil) |
| 7.1 | 20 | 0.30 |
| 7.2 | 60 | 0.93 |
| 7.3 | 20 | 0.30 |

Example 14

Multi-Layer Film Properties

The formulation and process of a multi-layer film in accordance with Example 13 was evaluated. The co-extruded film as described in Example 13 was found to have the properties described in Table 14. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 14

| Multi-layer film characteristics | | |
|---|---|---|
| Physical Properties | Units | Film 7 |
| Layering | | 20/60/20 |
| Color | | White |
| Gauge | mil | 1.508 |
| Basis Weight | g/m$^2$ | 36.2 |
| Light Transmission | % | 42.9 |
| COF, Kinetic - In\In | — | 0.152 |
| COF, Kinetic - Out\Out | — | 0.146 |
| Stress @ Peak MD | PSI | 7052 |
| Strain @ Peak MD | % | 514 |
| Stress @ 5% Strain MD | PSI | 2019 |
| Stress @ 10% Strain MD | PSI | 2456 |
| Stress @ 25% Strain MD | PSI | 2718 |
| Secant Modulus MD (1%) | PSI | 70058 |
| Elmendorf Tear MD Arm | g | 200 |
| Elmendorf Tear MD | gf | 40.7 |
| Stress @ Peak TD | PSI | 5470 |
| Strain @ Peak TD | % | 698 |
| Stress @ 5% Strain TD | PSI | 2051 |
| Stress @ 10% Strain TD | PSI | 2322 |
| Stress @ 25% Strain TD | PSI | 2078 |
| Secant Modulus TD (1%) | PSI | 70550 |
| Elmendorf Tear TD Arm | g | 1600 |
| Elmendorf Tear TD | gf | 870.4 |

TABLE 14-continued

| Multi-layer film characteristics | | |
|---|---|---|
| Physical Properties | Units | Film 7 |
| Dart Drop (26") | g | 266 |
| Slow Puncture - ¼" (D3) | gf | 1854 |

Example 15

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 15 to correlate the layer composition with the layer thickness. The instant example is provided to evaluate the properties of the exemplary multi-layer film.

A first- and a second-seal layer (8.1, 8.3) each comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (8.2) comprises Braskem INSPIRE™ 114 and ExxonMobil™ Exceed™ XP8656 Ampacet 10090P was added as a slip agent and Ampacet 111017P masterbatch was added. The percentages by weight of the components were about:

| | |
|---|---|
| 50% | Braskem INSPIRE ™ 114 |
| 33% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The resin was added to an extruder hopper. The resin was then heated in the extruder to form a molten material.

The molten materials described above were co-extruded and blown to form a multi-layer film with a gauge of 1.5 mils, a density of 0.963 g/cm$^3$, and with layer thicknesses as described in Table 15.

TABLE 15

| Target Layer Thicknesses | | |
|---|---|---|
| Layer | Thickness (%) | Thickness (mil) |
| 8.1 | 20 | 0.30 |
| 8.2 | 60 | 0.93 |
| 8.3 | 20 | 0.30 |

Example 16

Multi-Layer Film Properties

The formulation and process of a multi-layer film in accordance with Example 15 was evaluated. The co-extruded film as described in Example 15 was found to have the properties described in Table 16. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 16

| Multi-layer film characteristics | | |
|---|---|---|
| Physical Properties | Units | Film 8 |
| Layering | | 20/60/20 |
| Color | | White |
| Gauge | mil | 1.60 |
| Basis Weight | g/m$^2$ | 37.1 |
| Light Transmission | % | 41.8 |
| COF, Kinetic - In\In | — | 0.154 |
| COF, Kinetic - Out\Out | — | 0.153 |
| Stress @ Peak MD | PSI | 6113 |
| Strain @ Peak MD | % | 530 |
| Stress @ 5% Strain MD | PSI | 2220 |
| Stress @ 10% Strain MD | PSI | 2623 |
| Stress @ 25% Strain MD | PSI | 2765 |
| Secant Modulus MD (1%) | PSI | 79233 |
| Elmendorf Tear MD Arm | g | 200 |
| Elmendorf Tear MD | gf | 37.3* |
| Stress @ Peak TD | PSI | 5192 |
| Strain @ Peak TD | % | 720 |
| Stress @ 5% Strain TD | PSI | 2046 |
| Stress @ 10% Strain TD | PSI | 2283 |
| Stress @ 25% Strain TD | PSI | 2061 |
| Secant Modulus TD (1%) | PSI | 76103 |
| Elmendorf Tear TD Arm | g | 1600 |
| Elmendorf Tear TD | gf | 617.3 |
| Dart Drop (26") | g | 241 |
| Slow Puncture - ¼" (D3) | gf | 1738 |

Example 17

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 17 to correlate the layer composition with the layer thickness. The instant example is provided to evaluate the properties of the exemplary multi-layer film.

A first- and a second-seal layer (9.1, 9.3) each comprises ExxonMobil™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (9.2) comprises Total Petrochemicals 4170 and ExxonMobil™ Exceed™ XP8656 Ampacet 10090P was added as a slip agent and Ampacet 111017P masterbatch was added. The percentages by weight of the components were about:

| | |
|---|---|
| 55% | Total Petrochemicals 4170 |
| 23% | ExxonMobil ™ Exceed ™ XP8656 |
| 2% | Ampacet 10090P |
| 20% | Ampacet 111017P |

The resins, the slip agent, and the masterbatch were added to an extruder hopper and combined via blending to provide a formulation. The formulation was then heated in the extruder to form a molten material.

The resin was added to an extruder hopper. The resin was then heated in the extruder to form a molten material.

The molten materials described above were co-extruded and blown to form multi-layer film 9 with a gauge of 1 mil, a density of 0.980 g/cm$^3$, and with layer thicknesses as described in Table 17.

TABLE 17

| Target Layer Thicknesses | | |
|---|---|---|
| Layer | Thickness (%) | Thickness (mil) |
| 9.1 | 20 | 0.3 |
| 9.2 | 60 | 0.4 |
| 9.3 | 20 | 0.3 |

Example 18

Multi-Layer Film Properties

The formulation and process of a multi-layer film in accordance with Example 17 was evaluated. The co-extruded film as described in Example 17 was found to have the properties described in Table 18. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 18

| Multi-layer film characteristics | | |
|---|---|---|
| Physical Properties | Units | Film 9 |
| Layering | | 20/60/20 |
| Color | | White |
| Gauge | mil | 0.97 |
| Basis Weight | g/m$^2$ | 24.1 |
| Light Transmission | % | 60.4 |
| COF, Kinetic - In\In | — | 0.132 |
| COF, Kinetic - Out\Out | — | 0.437 |
| Stress @ Peak MD | PSI | 6765 |
| Strain @ Peak MD | % | 411 |
| Stress @ 5% Strain MD | PSI | 1548 |
| Stress @ 10% Strain MD | PSI | 1941 |
| Stress @ 25% Strain MD | PSI | 2395 |
| Secant Modulus MD (1%) | PSI | 46407 |
| Elmendorf Tear MD Arm | g | 200 |
| Elmendorf Tear MD | gf | 38.3* |
| Stress @ Peak TD | PSI | 4970 |
| Strain @ Peak TD | % | 686 |
| Stress @ 5% Strain TD | PSI | 1517 |
| Stress @ 10% Strain TD | PSI | 1698 |
| Stress @ 25% Strain TD | PSI | 1587 |
| Secant Modulus TD (1%) | PSI | 52241 |
| Elmendorf Tear TD Arm | g | 1600 |
| Elmendorf Tear TD | gf | 814.1 |
| Dart Drop (26") | g | 187 |
| Slow Puncture - 1/4" (D3) | gf | 874 |

Example 19

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 19 to correlate the layer composition with the layer thickness. The instant example is provided to evaluate the properties of the exemplary multi-layer film.

A first- and a second-seal layer (10.1, 10.3) each comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (10.2) comprises Total Petrochemicals 4170 and ExxonMobil™ Exceed™ XP8656 Ampacet 10090P was added as a slip agent and Ampacet 111017P masterbatch was added. The percentages by weight of the components were about:

| | |
|---|---|
| 55% | Total Petrochemicals 4170 |
| 23% | ExxonMobil ™ Exceed ™ XP8656 |
| 2% | Ampacet 10090P |
| 20% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form a multi-layer film 10 with a gauge of 1.25 mils, a density of 0.949 g/cm$^3$, and with layer thicknesses as described in Table 19.

TABLE 19

| Target Layer Thicknesses | | |
|---|---|---|
| Layer | Thickness (%) | Thickness (mil) |
| 10.1 | 30 | 0.375 |
| 10.2 | 40 | 0.5 |
| 10.3 | 30 | 0.375 |

Example 20

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 20 to correlate the layer composition with the layer thickness. The instant example is provided to evaluate the properties of the exemplary multi-layer film.

A first- and a second-seal layer (11.1, 11.3) each comprises Nova Chemicals® SCLAIR® FP120A and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58.25% | Nova Chemicals ® SCLAIR ® FP120A |
| 38% | ExxonMobil ™ LDPE LD 306.57 |
| 1.75% | Ampacet 10090P |
| 2.0% | Polyfil ABC5000HC |

The resins, the slip agent, and the antiblock were added to an extruder hopper and combined via blending to provide a formulation. The formulation was then heated in the extruder to form a molten material.

A deformation-resistant layer (11.2) comprises DOW® ELITE™ 5960G and Nova Chemicals® SCLAIR® FP120A. Ampacet 10090P was added as a slip agent. The percentages by weight of the components were about:

| | |
|---|---|
| 36% | DOW ® ELITE ™ 5960G |
| 62.5% | Nova Chemicals ® SCLAIR ® FP120A |
| 1.5% | Ampacet 10090P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 11 with a gauge of 1.55 mils and with layer thicknesses as described in Table 20.

TABLE 20

| Target Layer Thicknesses | | |
|---|---|---|
| Layer | Thickness (%) | Thickness (mil) |
| 11.1 | 25 | 0.375 |
| 11.2 | 50 | 0.750 |
| 11.3 | 25 | 0.375 |

Example 21

Multi-Layer Film Properties

The formulation and process of a multi-layer film in accordance with Example 20 was evaluated. The co-extruded film as described in Example 20 was found to have the properties described in Table 21. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 21

| Multi-layer film characteristics | | |
|---|---|---|
| Physical Properties | Units | Film 11 |
| Color | | Clear |
| Gauge | mil | 1.62 |
| Light Transmission | % | — |
| COF, Kinetic - In\In | — | 0.153 |
| COF, Kinetic - Out\Out | — | 0.160 |
| Stress @ Peak MD | PSI | 4269 |
| Strain @ Peak MD | % | 671 |
| Stress @ Yield MD | PSI | 1860 |
| Strain @ Yield MD | % | 14 |
| Stress @ 5% Strain MD | PSI | 1380 |
| Stress @ 10% Strain MD | PSI | 1764 |
| Stress @ 25% Strain MD | PSI | 1917 |
| Secant Modulus MD (1%) | PSI | 42722 |
| Elmendorf Tear MD Arm | g | 400 |
| Elmendorf Tear MD | gf | 195 |
| Stress @ Peak TD | PSI | 3371 |
| Strain @ Peak TD | % | 944 |
| Stress @ Yield TD | PSI | 2011 |
| Strain @ Yield TD | % | 14 |
| Stress @ 5% Strain TD | PSI | 1637 |
| Stress @ 10% Strain TD | PSI | 1997 |

TABLE 21-continued

| Multi-layer film characteristics | | |
|---|---|---|
| Physical Properties | Units | Film 11 |
| Stress @ 25% Strain TD | PSI | 1829 |
| Secant Modulus TD (1%) | PSI | 54068 |
| Elmendorf Tear TD Arm | g | 3200 |
| Elmendorf Tear TD | gf | 1469 |
| Dart Drop (26") | g | 135 |
| § Slow Puncture - ¼" (D3) | gf | 1460 |

Example 22

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 22 to correlate the layer composition with the layer thickness. The instant example is provided to evaluate the properties of the exemplary multi-layer film.

A first- and a second-seal layer (12.1, 12.3) each comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ XP 8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (12.2) comprises DOW® ELITE™ 5960G and ExxonMobil™ Exceed™ XP8656 as the base resins Ampacet 10090P was added as a slip agent and Ampacet 111017P masterbatch was added. The percentages by weight of the components were about:

| | |
|---|---|
| 62% | DOW ® ELITE ™ 5960G |
| 21% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 12 with a gauge of 1.5 mils, a density of 0.967 g/cm$^3$, and with layer thicknesses as described in Table 22.

TABLE 22

| Target Layer Thicknesses | | |
|---|---|---|
| Layer | Thickness (%) | Thickness (mil) |
| 12.1 | 30 | 0.45 |
| 12.2 | 40 | 0.6 |
| 12.3 | 30 | 0.45 |

Example 23

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 23 to correlate the layer composition with the layer thickness. The instant example is provided to evaluate the properties of the exemplary multi-layer film.

A first- and a second-seal layer (13.1, 13.3) each comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ XP 8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (13.2) comprises DOW® ELITE™ 5960G and ExxonMobil™ Exceed™ XP8656 as the base resins Ampacet 10090P was added as a slip agent and Ampacet 111017P masterbatch was added. The percentages by weight of the components were about:

| | |
|---|---|
| 62% | DOW ® ELITE ™ 5960G |
| 21% | ExxonMobil ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 13 with a gauge of 1.75 mils, a density of 0.967 g/cm$^3$, and with layer thicknesses as described in Table 23.

TABLE 23

| Target Layer Thicknesses | | |
|---|---|---|
| Layer | Thickness (%) | Thickness (mil) |
| 13.1 | 30 | 0.525 |
| 13.2 | 40 | 0.7 |
| 13.3 | 30 | 0.525 |

Example 24

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 24 to correlate the layer composition with the layer thickness. The instant example is provided to evaluate the properties of the exemplary multi-layer film.

Each of a first- and a second-seal layer (14.1, 14.3) comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ XP 8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (14.2) comprises DOW® ELITE™ 5960G and ExxonMobil™ Exceed™ XP8656 as the base resins Ampacet 10090P was added as a slip agent and Ampacet 111017P masterbatch was added. The percentages by weight of the components were about:

| | |
|---|---|
| 62% | DOW ® ELITE ™ 5960G |
| 21% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 14 with a gauge of 1 mil, a density of 0.967 g/cm$^3$, and with layer thicknesses as described in Table 24.

TABLE 24

| Target Layer Thicknesses | | |
|---|---|---|
| Layer | Thickness (%) | Thickness (mil) |
| 14.1 | 30 | 0.3 |
| 14.2 | 40 | 0.4 |
| 14.3 | 30 | 0.3 |

Example 25

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 25 to correlate the layer composition with the layer thickness. The instant example is provided to evaluate the properties of the exemplary multi-layer film.

Each of a first- and a second-seal layer (15.1, 15.3) comprises ExxonMobil™ Exceed™ 8318 and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58% | ExxonMobil ™ Exceed ™ 8318 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (15.2) comprises DOW® ELITE™ 5960G and ExxonMobil™ Exceed™ 8318 as the base resins Ampacet 10090P was added as a slip agent and Ampacet 111017P masterbatch was added. The percentages by weight of the components were about:

| | |
|---|---|
| 62% | DOW ® ELITE ™ 5960G |
| 21% | ExxonMobil ™ Exceed ™ 8318 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 15 with a gauge of 1.5 mils, a density of 0.968 g/cm$^3$, and with layer thicknesses as described in Table 25.

TABLE 25

| Target Layer Thicknesses | | |
|---|---|---|
| Layer | Thickness (%) | Thickness (mil) |
| 15.1 | 30 | 0.45 |
| 15.2 | 40 | 0.6 |
| 15.3 | 30 | 0.45 |

Example 26

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 26 to correlate the layer composition with the layer thickness. The instant example is provided to evaluate the properties of the exemplary multi-layer film.

Each of a first- and a second-seal layer (16.1, 16.3) comprises ExxonMobil™ Exceed™ 8318 and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58% | ExxonMobil ™ Exceed ™ 8318 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (16.2) comprises DOW® ELITE™ 5960G and ExxonMobil™ EXT318A as the base resins Ampacet 10090P was added as a slip agent and Ampacet 111017P masterbatch was added. The percentages by weight of the components were about:

| | |
|---|---|
| 62% | DOW ® ELITE ™ 5960G |
| 21% | ExxonMobil ™ Exceed ™ 8318 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 16 with a gauge of 1.75 mils, a density of 0.968 g/cm$^3$, and with layer thicknesses as described in Table 26.

TABLE 26

| Target Layer Thicknesses | | |
|---|---|---|
| Layer | Thickness (%) | Thickness (mil) |
| 16.1 | 30 | 0.525 |
| 16.2 | 40 | 0.7 |
| 16.3 | 30 | 0.525 |

Example 27

Heat Seal Strength

Figure 3:
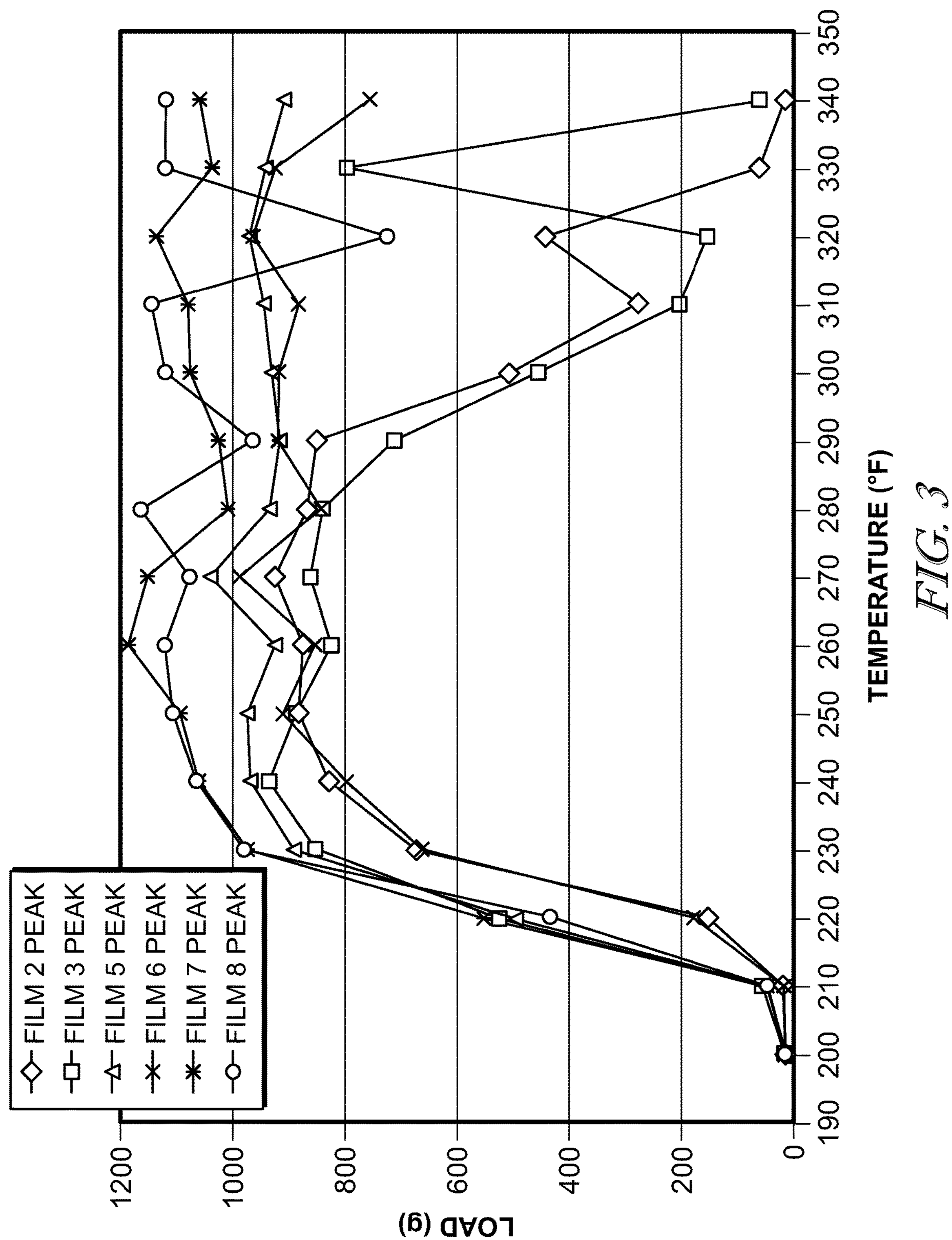
FIG. 3 is a graph of heat-seal strength of exemplary multi-layer films.
Figure 4:
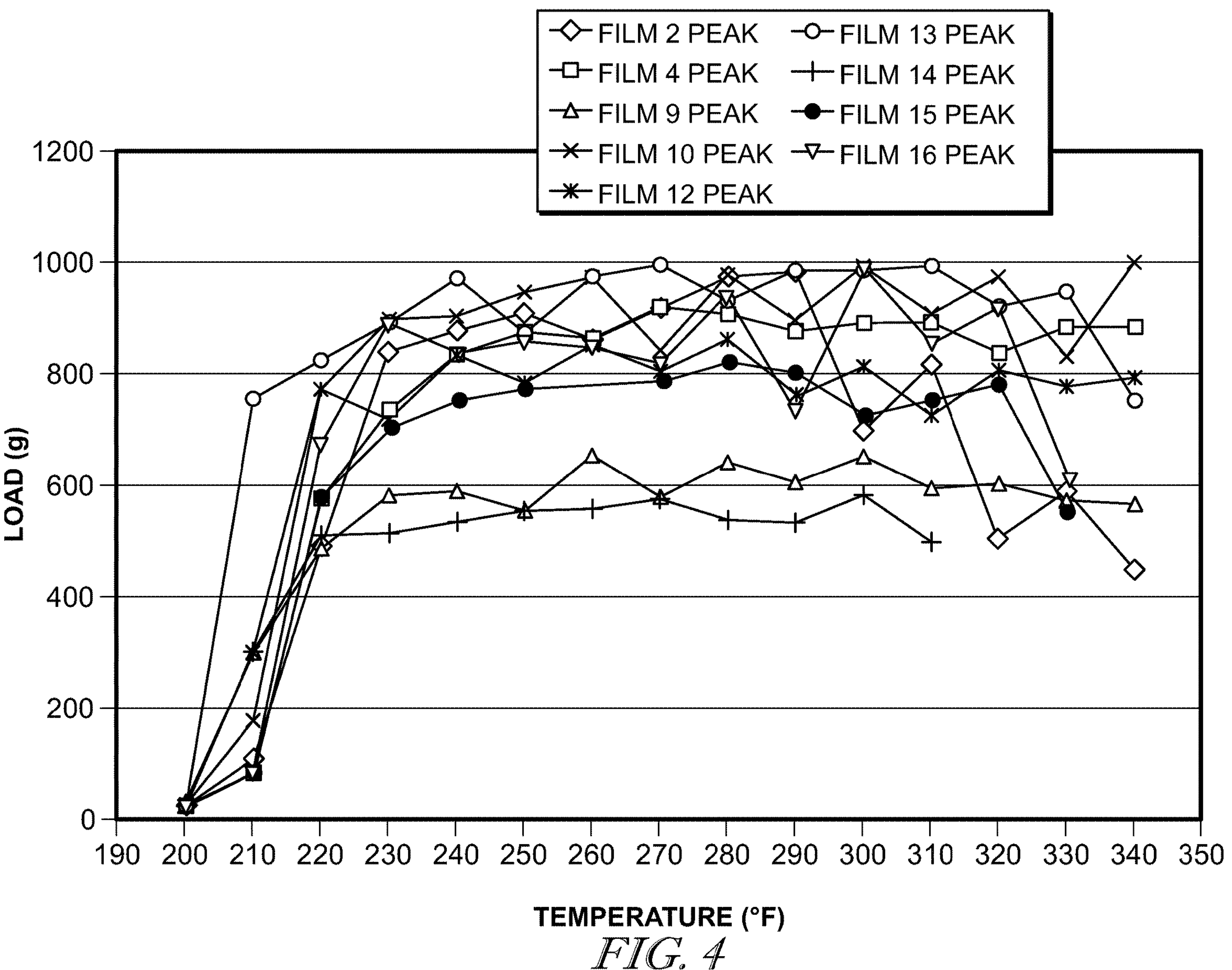
FIG. 4 is a graph similar to FIG. 3 showing heat-seal strength of exemplary multi-layer films.

Exemplary multi-layer films 2, 3, 4, 5, 6, 7, 8, 9, 10, 12, 13, 14, 15, and 16 were analyzed for heat seal strength. The exemplary multi-layer films were tested on a Hudson-Sharp Bagger with a jaw pressure of 60 PSI, a test speed of 30 cm/min, a dwell time of 1000 ms, and a cooling time of 10 s. The seal temperature was increased in 10° F. increments from 200° F. to 340° F. and the seal strength (g) was measured for each indicated temperature, as shown in Tables 27 and 28, and FIGS. 3 and 4. Peeling is defined as the two sealing layers separating at the sealing interface. Breaking is defined as the seal fracturing. Burn through is defined as when the jaws burn through the film.

TABLE 27

| Heat Seal values for exemplary multi-layer | | | | | | |
|---|---|---|---|---|---|---|
| Temp ° F. | Film 2 Load (g) | Film 3 Load (g) | Film 5 Load (g) | Film 6 Load (g) | Film 7 Load (g) | Film 8 Load (g) |
| 200 | −1* | 18* | 18* | 9* | 20* | 16* |
| 210 | 19* | 55* | 52* | 18* | 52* | 48* |
| 220 | 152* | 524* | 497* | 178* | 552* | 435* |
| 230 | 672* | 853 | 891* | 664* | 974* | 980* |
| 240 | 828 | 936 | 969 | 797 | 1062* | 1066* |
| 250 | 879 | 889 | 975 | 911 | 1095 | 1107 |
| 260 | 873 | 825 | 924 | 854 | 1189 | 1121 |
| 270 | 923 | 862 | 1039 | 987 | 1153 | 1078 |
| 280 | 866 | 839 | 934 | 843 | 1010 | 1162 |
| 290 | 850 | 713# | 916 | 919 | 1027 | 965 |
| 300 | 508# | 455# | 931 | 918 | 1077 | 1121 |
| 310 | 277# | 204# | 945 | 883 | 1081 | 1145 |
| 320 | 443# | 153# | 970 | 963 | 1137 | 725 |
| 330 | 61# | 796# | 941 | 925 | 1038 | 1121 |
| 340 | 16** | 61** | 909 | 756 | 1060 | 1120 |

*denotes failure from peeling denotes failure from breaking

**denotes failure from burn through

TABLE 28

| Heat Seal values for exemplary multi-layer films | | | | | | | | | |
|---|---|---|---|---|---|---|---|---|---|
| Temp ° F. | Film 2 Load (g) | Film 4 Load (g) | Film 9 Load (g) | Film 10 Load (g) | Film 12 Load (g) | Film 13 Load (g) | Film 14 Load (g) | Film 15 Load (g) | Film 16 Load (g) |
| 200 | 20 | 25 | 33 | 31 | 29 | 32 | 48 | 20 | 27 |
| 210 | 106 | 84 | 305 | 176 | 300 | 755 | 301 | 76 | 83 |
| 220 | 489 | 574 | 489 | 769 | 771 | 824 | 511 | 581 | 676 |
| 230 | 837 | 735 | 580 | 897 | 718 | 891 | 512 | 701 | 890 |
| 240 | 877 | 834 | 589 | 901 | 832 | 970 | 533 | 750 | 840 |
| 250 | 907 | 873 | 555 | 945 | 782 | 871 | 554 | 773 | 856 |
| 260 | 859 | 863 | 652 | 973 | 848 | 973 | 558 | 780 | 846 |
| 270 | 913 | 918 | 577 | 840 | 803 | 993 | 576 | 785 | 817 |
| 280 | 970 | 905 | 641 | 975 | 860 | 931 | 538 | 819 | 943 |
| 290 | 975 | 875 | 602 | 896 | 762 | 984 | 532 | 802 | 730 |
| 300 | 697 | 891 | 652 | 992 | 812 | 983 | 581** | 725 | 988 |
| 310 | 816 | 80 | 594 | 907 | 725 | 992 | 497** | 750 | 855 |
| 320 | 505 | 837 | 601 | 973 | 805 | 917 | | 781 | 916 |
| 330 | 589 | 882 | 571# | 830 | 777 | 946 | | 552# | 610** |
| 340 | 447** | 883 | 567** | 997 | 793# | 751** | | | |

denotes failure from breaking

**denotes failure from burn through

Example 28

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 29 to correlate the layer composition with the layer thickness. The instant example is provided to evaluate the properties of the exemplary multi-layer film.

Each of a first- and a second-seal layer (17.1, 17.3) comprises is ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (17.2) comprises Total Petrochemicals 4170 and ExxonMobil™ Exceed™ XP8656 as the base resins Ampacet 10090P was added as a slip agent and Ampacet 111017P masterbatch was added. The percentages by weight of the components were about:

| | |
|---|---|
| 60% | Total Petrochemicals 4170 |
| 23% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 17 with a gauge of 1.75 mils, a density of 0.961 g/cm$^3$, and with layer thicknesses as described in Table 29.

TABLE 29

| Target Layer Thicknesses | | |
|---|---|---|
| Layer | Thickness (%) | Thickness (mil) |
| 17.1 | 20 | 0.35 |
| 17.2 | 60 | 1.05 |
| 17.3 | 20 | 0.35 |

Example 29

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 30 to correlate the layer composition with the layer thickness. The instant example is provided to evaluate the properties of the exemplary multi-layer film.

Each of a first- and a second-seal layer (18.1, 18.3) comprises ExxonMobil™ Exceed™ 8318 and ExxonMobil™ LDPE LD 306.57 as the base resins. Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (18.2) comprises Braskem INSPIRE™ 114 and ExxonMobil™ Exceed™ XP8656 as the base resins Ampacet 10090P was added as a slip agent and Ampacet 111017P masterbatch was added. The percentages by weight of the components were about:

| | |
|---|---|
| 62% | Braskem INSPIRE ™ 114 |
| 21% | ExxonMobil ™ Exceed ™ XP8656 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 18 with a gauge of 1.75 mils, a density of 0.968 g/cm$^3$, and with layer thicknesses as described in Table 30.

TABLE 30

| Target Layer Thicknesses | | |
|---|---|---|
| Layer | Thickness (%) | Thickness (mil) |
| 18.1 | 20 | 0.35 |
| 18.2 | 60 | 1.05 |
| 18.3 | 20 | 0.35 |

Example 30

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 31 to correlate the layer composition with the layer thickness. The instant example is provided to evaluate the properties of the exemplary multi-layer film.

Each of a first- and a second-seal layer (19.1, 19.3) comprises Nova Chemicals® SCLAIR® FP120A and ExxonMobil™ LDPE LD 306.57 as the base resins. Ampacet 10090P was added as a slip agent, Polyfil ABC5000HC was added as an antiblock agent, and Ampacet 101140 was added as an antistatic agent. The percentages by weight of the components were about:

| | |
|---|---|
| 51.25% | Nova Chemicals ® SCLAIR ® FP120A |
| 38% | ExxonMobil ™ LDPE LD 306.57 |
| 1.75% | Ampacet 10090P |
| 4% | Polyfil ABC5000HC |
| 5% | Ampacet 101140 |

The resins, the slip agent, the antiblock, and the antistatic were added to an extruder hopper and combined via blending to provide a formulation. The formulation was then heated in the extruder to form a molten material.

A deformation-resistant layer (19.2) comprises DOW® ELITE™ 5960G and Nova Chemicals® SCLAIR® FP120A as the base resins Ampacet 10090P was added as a slip agent and Ampacet 111017P masterbatch was added. The percentages by weight of the components were about:

| | |
|---|---|
| 36% | DOW ® ELITE ™ 5960G |
| 61.5% | Nova Chemicals ® SCLAIR ® FP120A |
| 1.5% | Ampacet 10090P |
| 1% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form multi-layer film 19 with a gauge of 1.5 mils, a density of 0.968 g/cm$^3$, and with layer thicknesses as described in Table 31.

TABLE 31

| Target Layer Thicknesses | | |
|---|---|---|
| Layer | Thickness (%) | Thickness (mil) |
| 19.1 | 25 | 0.375 |
| 19.2 | 50 | 0.75 |
| 19.3 | 25 | 0.375 |

Example 31

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 32 to correlate the layer composition with the layer thickness. The instant example is provided to evaluate the properties of the exemplary multi-layer film.

Each of a first- and a second-seal layer (20.1, 20.3) comprises ExxonMobil™ Exceed™ XP8656 and ExxonMobil™ LDPE LD 306.57 as the base resins Ampacet 10090P was added as a slip agent, Polyfil ABC5000HC was added as an antiblock agent, and Ampacet 101140 was added as an antistatic agent. The percentages by weight of the components were about:

| | |
|---|---|
| 51.25% | ExxonMobil ™ Exceed ™ XP8656 |
| 38% | ExxonMobil ™ LDPE LD 306.57 |
| 1.75% | Ampacet 10090P |
| 4% | Polyfil ABC5000HC |
| 5% | Ampacet 101140 |

The resins, the slip agent, the antiblock, and the antistatic were added to an extruder hopper and combined via blending to provide a formulation. The formulation was then heated in the extruder to form a molten material.

A deformation-resistant layer (20.2) comprises Total Petrochemicals 4170 and ExxonMobil™ Exceed™ XP8656 as the base resins Ampacet 10090P was added as a slip agent and Ampacet 101140 was added as an antistatic agent. The percentages by weight of the components were about:

| | |
|---|---|
| 60% | Total Petrochemicals 4170 |
| 37.25% | ExxonMobil ™ Exceed ™ XP8656 |
| 1.75% | Ampacet 10090P |
| 1% | Ampacet 101140 |

The resins, the slip agent, and the antistatic were added to an extruder hopper and combined via blending to provide a formulation. The formulation was then heated in the extruder to form a molten material.

The molten materials described above were co-extruded and blown to form multi-layer film 20 with a gauge of 1.5 mils, a density of 0.915 g/cm$^3$, and with layer thicknesses as described in Table 32.

TABLE 32

| Target Layer Thicknesses | | |
|---|---|---|
| Layer | Thickness (%) | Thickness (mil) |
| 20.1 | 20 | 0.3 |
| 20.2 | 60 | 0.9 |
| 20.3 | 20 | 0.3 |

Multi-Layer Film Properties

Co-extruded multi-layer film 20 was found to have the properties described in Table 33. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 33

| Multi-layer film characteristics | | |
|---|---|---|
| Physical Properties | Units | Film 20 |
| Gauge | mil | 1.78 |
| Haze | % | 15.9 |
| COF, Static - In\In | — | 0.253 |
| COF, Static - Out\Out | — | 0.397 |
| COF, Kinetic - In\In | — | 0.247 |
| COF, Kinetic - Out\Out | — | 0.298 |

TABLE 33-continued

| Multi-layer film characteristics | | |
|---|---|---|
| Physical Properties | Units | Film 20 |
| Tensile Gauge MD | mil | 1.80 |
| Stress @ Peak MD | PSI | 6,193 |
| Strain @ Peak MD | % | 531 |
| Stress @ Break MD | PSI | 6,193 |
| Strain @ Break MD | % | 531 |
| Stress @ Yield MD | PSI | 2,216 |
| Strain @ Yield MD | % | 14 |
| Stress @ 5% Strain MD | PSI | 1,667 |
| Stress @ 10% Strain MD | PSI | 2,088 |
| Stress @ 25% Strain MD | PSI | 2,412 |
| Stress @ 50% Strain MD | PSI | 2,634 |
| Stress @ 100% Strain MD | PSI | 2,700 |
| Secant Modulus MD (1%) | PSI | 53,871 |
| TEA MD | FtLb/in$^2$ | 3,226 |
| Elmendorf Tear MD Arm | g | 400 |
| Elmendorf Tear MD | gf | 127 |
| Tensile Gauge TD | mil | 1.59 |
| Stress @ Peak TD | PSI | 4,954 |
| Strain @ Peak TD | % | 681 |
| Stress @ Break TD | PSI | 4,953 |
| Strain @ Break TD | % | 682 |
| Stress @ Yield TD | PSI | 2,018 |
| Strain @ Yield TD | % | 12 |
| Stress @ 5% Strain TD | PSI | 1,688 |
| Stress @ 10% Strain TD | PSI | 1,987 |
| Stress @ 25% Strain TD | PSI | 1,973 |
| Stress @ 50% Strain TD | PSI | 1,825 |
| Stress @ 100% Strain TD | PSI | 1,833 |
| Secant Modulus TD (1%) | PSI | 54,639 |
| TEA TD | FtLb/in$^2$ | 2,945 |
| Elmendorf Tear TD Arm | g | 1,600 |
| Elmendorf Tear TD | gf | 765 |
| Dart Drop (26") | g | 266 |
| § Slow Puncture - ¼" (D3) | gf | 1,403 |

Example 32

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 34 to correlate the layer composition with the layer thickness. The instant example is provided to evaluate the properties of the exemplary multi-layer film.

Each of a first- and a second-seal layer (21.1, 21.3) comprises NOVA Chemicals Surpass® FPs016-C Octene sLLDPE and ExxonMobil™ LDPE LD 306.57 as the base resins Ampacet 10090P was added as a slip agent, Polyfil ABC5000HC was added as an antiblock agent, and Ampacet 101140 was added as an antistatic agent. The percentages by weight of the components were about:

| | |
|---|---|
| 51.25% | NOVA Chemicals Surpass ® FPs016-C Octene sLLDPE |
| 38% | ExxonMobil ™ LDPE LD 306.57 |
| 1.75% | Ampacet 10090P |
| 4% | Polyfil ABC5000HC |
| 5% | Ampacet 101140 |

The resins, the slip agent, the antiblock, and the antistatic were added to an extruder hopper and combined via blending to provide a formulation. The formulation was then heated in the extruder to form a molten material.

A deformation-resistant layer (21.2) comprises Total Petrochemicals 4170 and NOVA Chemicals Surpass® FPs016-C Octene sLLDPE as the base resins Ampacet 10090P was added as a slip agent and Ampacet 101140 was added as an antistatic agent. The percentages by weight of the components were about:

| | |
|---|---|
| 60% | Total Petrochemicals 4170 |
| 37.25% | NOVA Chemicals Surpass ® FPs016-C Octene sLLDPE |
| 1.75% | Ampacet 10090P |
| 1% | Ampacet 101140 |

The resins, the slip agent, and the masterbatch were added to an extruder hopper and combined via blending to provide a formulation. The formulation was then heated in the extruder to form a molten material.

The molten materials described above were co-extruded and blown to form multi-layer film 21 with a gauge of 1.5 mils, a density of 0.915 g/cm$^3$, and with layer thicknesses as described in Table 34.

TABLE 34

| Target Layer Thicknesses | | |
|---|---|---|
| Layer | Thickness (%) | Thickness (mil) |
| 21.1 | 20 | 0.3 |
| 21.2 | 60 | 0.9 |
| 21.3 | 20 | 0.3 |

Co-extruded multi-layer film 21 was found to have the properties described in Table 35. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 35

| Multi-layer film characteristics | | |
|---|---|---|
| Physical Properties | Units | Film 21 |
| Gauge | mil | 1.50 |
| Haze | % | 15.3 |

TABLE 35-continued

| Multi-layer film characteristics | | |
|---|---|---|
| Physical Properties | Units | Film 21 |
| COF, Static - In\In | — | 0.280 |
| COF, Static - Out\Out | — | 0.260 |
| COF, Kinetic - In\In | — | 0.263 |
| COF, Kinetic - Out\Out | — | 0.256 |
| Tensile Gauge MD | mil | 1.55 |
| Stress @ Peak MD | PSI | 6,145 |
| Strain @ Peak MD | % | 530 |
| Stress @ Break MD | PSI | 6,145 |
| Strain @ Break MD | % | 530 |
| Stress @ Yield MD | PSI | 2,133 |
| Strain @ Yield MD | % | 14 |
| Stress @ 5% Strain MD | PSI | 1,572 |
| Stress @ 10% Strain MD | PSI | 1,988 |
| Stress @ 25% Strain MD | PSI | 2,338 |
| Stress @ 50% Strain MD | PSI | 2,607 |
| Stress @ 100% Strain MD | PSI | 2,743 |
| Secant Modulus MD (1%) | PSI | 46,872 |
| TEA MD | FtLb/in$^2$ | 3,235 |
| Elmendorf Tear MD Arm | g | 200 |
| Elmendorf Tear MD | gf | 52 |
| Tensile Gauge TD | mil | 1.62 |
| Stress @ Peak TD | PSI | 5,024 |
| Strain @ Peak TD | % | 753 |
| Stress @ Break TD | PSI | 5,024 |
| Strain @ Break TD | % | 753 |
| Stress @ Yield TD | PSI | 1,956 |
| Strain @ Yield TD | % | 13 |
| Stress @ 5% Strain TD | PSI | 1,600 |
| Stress @ 10% Strain TD | PSI | 1,914 |
| Stress @ 25% Strain TD | PSI | 1,918 |
| Stress @ 50% Strain TD | PSI | 1,798 |
| Stress @ 100% Strain TD | PSI | 1,765 |
| Secant Modulus TD (1%) | PSI | 47,378 |
| TEA TD | FtLb/in$^2$ | 3,275 |
| Elmendorf Tear TD Arm | g | 1,600 |
| Elmendorf Tear TD | gf | 679 |
| Dart Drop (26") | g | 258 |
| § Slow Puncture - ¼" (D3) | gf | 1,278 |

Example 33

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 36 to correlate the layer composition with the layer thickness. The instant example is provided to evaluate the properties of the exemplary multi-layer film.

Each of a first- and a second-seal layer (22.1, 22.3) comprises ExxonMobil™ Exceed™ XP8656 and ExxonMobil™ LDPE LD 306.57 as the base resins Ampacet 10090P was added as a slip agent, Polyfil ABC5000HC was added as an antiblock agent, and Ampacet 101140 was added as an antistatic agent. The percentages by weight of the components were about:

| | |
|---|---|
| 51.25% | ExxonMobil ™ Exceed ™ XP8656 |
| 38% | ExxonMobil ™ LDPE LD 306.57 |
| 1.75% | Ampacet 10090P |
| 4% | Polyfil ABC5000HC |
| 5% | Ampacet 101140 |

The resins, the slip agent, the antiblock, and the antistatic were added to an extruder hopper and combined via blending to provide a formulation. The formulation was then heated in the extruder to form a molten material.

A deformation-resistant layer (22.2) comprises LyondellBasell Pro-fax 7823 and ExxonMobil™ Exceed™ XP8656 as the base resins. Ampacet 10090P was added as a slip agent and Ampacet 101140 was added as an antistatic agent. The percentages by weight of the components were about:

| | |
|---|---|
| 60% | LyondellBasell Pro-fax 7823 |
| 37.25% | ExxonMobil ™ Exceed ™ XP8656 |
| 1.75% | Ampacet 10090P |
| 1% | Ampacet 101140 |

The resins, the slip agent, and the antistatic were added to an extruder hopper and combined via blending to provide a formulation. The formulation was then heated in the extruder to form a molten material.

The molten materials described above were co-extruded and blown to form multi-layer film 22 with a gauge of 1.5 mils, a density of 0.915 g/cm$^3$, and with layer thicknesses as described in Table 36.

TABLE 36

| Target Layer Thicknesses | | |
|---|---|---|
| Layer | Thickness (%) | Thickness (mil) |
| 22.1 | 20 | 0.3 |
| 22.2 | 60 | 0.9 |
| 22.3 | 20 | 0.3 |

Co-extruded multi-layer film 22 was found to have the properties described in Table 37. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 37

| Multi-layer film characteristics | | |
|---|---|---|
| Physical Properties | Units | Film 22 |
| Gauge | mil | 1.49 |
| Haze | % | 15.1 |
| COF, Static - In\In | — | 0.327 |
| COF, Static - Out\Out | — | 0.293 |
| COF, Kinetic - In\In | — | 0.280 |
| COF, Kinetic - Out\Out | — | 0.287 |
| Tensile Gauge MD | mil | 1.44 |
| Stress @ Peak MD | PSI | 6,849 |
| Strain @ Peak MD | % | 467 |
| Stress @ Break MD | PSI | 6,849 |
| Strain @ Break MD | % | 467 |
| Stress @ Yield MD | PSI | 2,437 |
| Strain @ Yield MD | % | 13 |
| Stress @ 5% Strain MD | PSI | 1,825 |
| Stress @ 10% Strain MD | PSI | 2,311 |
| Stress @ 25% Strain MD | PSI | 2,699 |
| Stress @ 50% Strain MD | PSI | 2,981 |
| Stress @ 100% Strain MD | PSI | 3,087 |
| Secant Modulus MD (1%) | PSI | 61,866 |
| TEA MD | FtLb/in$^2$ | 3,170 |
| Elmendorf Tear MD Arm | g | 200 |
| Elmendorf Tear MD | gf | 54 |
| Tensile Gauge TD | mil | 1.50 |
| Stress @ Peak TD | PSI | 4,981 |
| Strain @ Peak TD | % | 704 |
| Stress @ Break TD | PSI | 4,981 |
| Strain @ Break TD | % | 704 |
| Stress @ Yield TD | PSI | 2,068 |
| Strain @ Yield TD | % | 12 |
| Stress @ 5% Strain TD | PSI | 1,771 |
| Stress @ 10% Strain TD | PSI | 2,052 |
| Stress @ 25% Strain TD | PSI | 1,939 |
| Stress @ 50% Strain TD | PSI | 1,742 |
| Stress @ 100% Strain TD | PSI | 1,773 |
| Secant Modulus TD (1%) | PSI | 59,866 |
| TEA TD | FtLb/in$^2$ | 2,980 |
| Elmendorf Tear TD Arm | g | 1,600 |
| Elmendorf Tear TD | gf | 797 |
| Dart Drop (26") | g | 203 |
| § Slow Puncture - ¼" (D3) | gf | 1,242 |

Example 34

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 38 to correlate the layer composition with the layer thickness. The instant example is provided to evaluate the properties of the exemplary multi-layer film.

Each of a first- and a second-seal layer (23.1, 23.3) comprises ExxonMobil™ Exceed™ XP8656 and ExxonMobil™ LDPE LD 306.57 as the base resins Ampacet 10090P was added as a slip agent, Polyfil ABC5000HC was added as an antiblock agent, and Ampacet 101140 was added as an antistatic agent. The percentages by weight of the components were about:

| | |
|---|---|
| 51.25% | ExxonMobil ™ Exceed ™ XP8656 |
| 38% | ExxonMobil ™ LDPE LD 306.57 |
| 1.75% | Ampacet 10090P |
| 4% | Polyfil ABC5000HC |
| 5% | Ampacet 101140 |

The resins, the slip agent, the antiblock, and the antistatic were added to an extruder hopper and combined via blending to provide a formulation. The formulation was then heated in the extruder to form a molten material.

A deformation-resistant layer (23.2) comprises Braskem INSPIRE™ 114 and ExxonMobil™ EXT318A as the base resins Ampacet 10090P was added as a slip agent and Ampacet 111017P masterbatch was added. The percentages by weight of the components were about:

| | |
|---|---|
| 62% | Braskem INSPIRE ™ 114 |
| 21% | ExxonMobil ™ Exceed ™ 8318 |
| 2% | Ampacet 10090P |
| 15% | Ampacet 111017P |

The resins, the slip agent, and the masterbatch were added to an extruder hopper and combined via blending to provide a formulation. The formulation was then heated in the extruder to form a molten material.

The molten materials described above were co-extruded and blown to form a multi-layer film 23 with a gauge of 1.5 mils, a density of 0.915 g/cm$^3$, and with layer thicknesses as described in Table 38.

TABLE 38

| Target Layer Thicknesses | | |
|---|---|---|
| Layer | Thickness (%) | Thickness (mil) |
| 23.1 | 20 | 0.3 |
| 23.2 | 60 | 0.9 |
| 23.3 | 20 | 0.3 |

Co-extruded multi-layer film 23 was found to have the properties described in Table 39. Layering is the percentage thickness of each seal/deformation-resistant/first-seal layer. Color is the color of the film. Gauge is the thickness of the film measured in mils. Basis weight is a mass per unit measurement according to ASTM D646 and has units of g/m$^2$. Light transmission measures the percentage transmittance of light according to ATSM D1003. COF is a unitless measure of how slippery a film according to ASTM Method D1894. Stress is measures of tensile strength according to ASTM D882 and has a unit of PSI. Secant modulus is a measure of film stiffness according to ASTM D882 and has a unit of PSI. Elmendorf tear is a measure of the amount of weight required to propagate a tear according to ASTM D1922 and has a unit of gf. Dart drop is a measure of impact resistance according to ASTM D1709 and has units of grams. Slow puncture is a measure of penetration resistance according to ASTM F1306 and has the units of gram-force (gf).

TABLE 39

| Multi-layer film characteristics | | |
|---|---|---|
| Physical Properties | Units | Film 23 |
| Gauge | mil | 1.42 |
| Haze | % | 15.1 |
| COF, Static - In\In | — | 0.203 |
| COF, Static - Out\Out | — | 0.260 |
| COF, Kinetic - In\In | — | 0.209 |
| COF, Kinetic - Out\Out | — | 0.262 |
| Tensile Gauge MD | mil | 1.54 |
| Stress @ Peak MD | PSI | 5,968 |
| Strain @ Peak MD | % | 521 |
| Stress @ Break MD | PSI | 5,968 |
| Strain @ Break MD | % | 521 |
| Stress @ Yield MD | PSI | 2,583 |
| Strain @ Yield MD | % | 12 |
| Stress @ 5% Strain MD | PSI | 2,147 |
| Stress @ 10% Strain MD | PSI | 2,519 |
| Stress @ 25% Strain MD | PSI | 2,700 |
| Stress @ 50% Strain MD | PSI | 2,818 |
| Stress @ 100% Strain MD | PSI | 2,933 |
| Secant Modulus MD (1%) | PSI | 67,536 |
| TEA MD | FtLb/in$^2$ | 3,236 |
| Elmendorf Tear MD Arm | g | 200 |
| Elmendorf Tear MD | gf | 56 |
| Tensile Gauge TD | mil | 1.55 |
| Stress @ Peak TD | PSI | 5,276 |
| Strain @ Peak TD | % | 691 |
| Stress @ Break TD | PSI | 5,276 |
| Strain @ Break TD | % | 691 |
| Stress @ Yield TD | PSI | 2,271 |
| Strain @ Yield TD | % | 10 |
| Stress @ 5% Strain TD | PSI | 2,021 |
| Stress @ 10% Strain TD | PSI | 2,267 |
| Stress @ 25% Strain TD | PSI | 2,024 |
| Stress @ 50% Strain TD | PSI | 1,898 |
| Stress @ 100% Strain TD | PSI | 2,005 |
| Secant Modulus TD (1%) | PSI | 70,656 |
| TEA TD | FtLb/in$^2$ | 3,196 |
| Elmendorf Tear TD Arm | g | 1,600 |
| Elmendorf Tear TD | gf | 605 |
| Dart Drop (26") | g | 225 |
| § Slow Puncture - ¼" (D3) | gf | 1,624 |

Example 35

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 40 to correlate the layer composition with the layer thickness. The instant example is provided to evaluate the properties of the exemplary multi-layer film.

Each of a first- and a second-seal layer (24.1, 24.3) comprises ExxonMobil™ Exceed™ XP8656 and ExxonMobil™ LDPE LD 306.57 as the base resins Ampacet 10090P was added as a slip agent, Polyfil ABC5000HC was added as an antiblock agent, and Ampacet 104355-N was added as an antistatic agent. The percentages by weight of the components were about:

| | |
|---|---|
| 54.25% | ExxonMobil ™ Exceed ™ XP8656 |
| 38% | ExxonMobil ™ LDPE LD 306.57 |
| 1.75% | Ampacet 10090P |
| 4% | Polyfil ABC5000HC |
| 2% | Ampacet 104355-N |

The resins, the slip agent, the antiblock, and the antistatic agent were added to an extruder hopper and combined via blending to provide a formulation. The formulation was then heated in the extruder to form a molten material.

A deformation-resistant layer (24.2) comprises Total Petrochemicals 4170 and ExxonMobil™ Exceed™ XP8656 as the base resins Ampacet 10090P was added as a slip agent and Ampacet 104355-N was added as an antistatic agent. The percentages by weight of the components were about:

| | |
|---|---|
| 60% | Total Petrochemicals 4170 |
| 37.25% | ExxonMobil ™ Exceed ™ XP8656 |
| 1.75% | Ampacet 10090P |
| 1% | Ampacet 104355-N |

The resins, the slip agent, and the antistatic agent were added to an extruder hopper and combined via blending to provide a formulation. The formulation was then heated in the extruder to form a molten material.

The molten materials described above were co-extruded and blown to form multi-layer film 24 with a gauge of 1 mil, a density of 0.915 g/cm$^3$, and with layer thicknesses as described in Table 40.

TABLE 40

| Target Layer Thicknesses | | |
|---|---|---|
| Layer | Thickness (%) | Thickness (mil) |
| 24.1 | 20 | 0.2 |
| 24.2 | 60 | 0.6 |
| 24.3 | 20 | 0.2 |

Example 36

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 41 to correlate the layer composition with the layer thickness. The instant example is provided to evaluate the properties of the exemplary multi-layer film.

Each of a first- and a second-seal layer (25.1, 25.3) comprises ExxonMobil™ Exceed™ XP8656 and ExxonMobil™ LDPE LD 306.57 as the base resins Ampacet 10090P was added as a slip agent and Polyfil ABC5000HC was added as an antiblock agent. The percentages by weight of the components were about:

| | |
|---|---|
| 58% | ExxonMobil ™ Exceed ™ XP8656 |
| 38% | ExxonMobil ™ LDPE LD 306.57 |
| 2% | Ampacet 10090P |
| 2% | Polyfil ABC5000HC |

The resins, the slip agent, and the antiblock were added to an extruder hopper and combined via blending to provide a formulation. The formulation was then heated in the extruder to form a molten material.

A deformation-resistant layer (25.2) comprises Total Petrochemicals 4170 and ExxonMobil™ Exceed™ XP8656 as the base resins Ampacet 10090P was added as a slip agent and Ampacet 111017P masterbatch was added. The percentages by weight of the components were about:

| | |
|---|---|
| 60% | Total Petrochemicals 4170 |
| 23% | ExxonMobil ™ Exceed ™ XP8656 |
| 2% | Ampacet 10090P |
| 15% | Ampacet 111017P masterbatch |

The resins, the slip agent, and the masterbatch were added to an extruder hopper and combined via blending to provide a formulation. The formulation was then heated in the extruder to form a molten material.

The molten materials described above were co-extruded and blown to form multi-layer film 25 with a gauge of about 2 mils, a density of 0.961 g/cm$^3$, and with layer thicknesses as described in Table 41.

TABLE 41

| Target Layer Thicknesses | | |
|---|---|---|
| Layer | Thickness (%) | Thickness (mil) |
| 25.1 | 20 | 0.4 |
| 25.2 | 60 | 1.2 |
| 25.3 | 20 | 0.4 |

Example 37

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 42 to correlate the layer composition with the layer thickness. The instant example is provided to evaluate the properties of the exemplary multi-layer film.

Each of a first- and a second-seal layer (26.1, 26.3) comprises ExxonMobil™ Exceed™ XP8656 and ExxonMobil™ LDPE LD 306.57 as the base resins Ampacet 10090P was added as a slip agent, Polyfil ABC5000HC was added as an antiblock agent, and Ampacet 104355-N was added as an antistatic agent. The percentages by weight of the components were about:

| | |
|---|---|
| 54.25% | ExxonMobil ™ Exceed ™ XP8656 |
| 38% | ExxonMobil ™ LDPE LD 306.57 |
| 1.75% | Ampacet 10090P |
| 4% | Polyfil ABC5000HC |
| 2% | Ampacet 104355-N |

The resins, the slip agent, the antiblock, and the antistatic agent were added to an extruder hopper and combined via blending to provide a formulation. The formulation was then heated in the extruder to form a molten material.

A deformation-resistant layer (26.2) comprises Total Petrochemicals 4170 and ExxonMobil™ Exceed™ XP8656 as the base resins Ampacet 10090P was added as a slip agent and Ampacet 104355-N was added as an antistatic agent. The percentages by weight of the components were about:

| | |
|---|---|
| 60% | Total Petrochemicals 4170 |
| 37.25% | ExxonMobil ™ Exceed ™ XP8656 |
| 1.75% | Ampacet 10090P |
| 1% | Ampacet 104355-N |

The resins, the slip agent, and the antistatic agent were added to an extruder hopper and combined via blending to provide a formulation. The formulation was then heated in the extruder to form a molten material.

The molten materials described above were co-extruded and blown to form multi-layer film 26 with a gauge of about 1.25 mils, a density of 0.915 g/cm$^3$, and with layer thicknesses as described in Table 42.

TABLE 42

| Target Layer Thicknesses | | |
|---|---|---|
| Layer | Thickness (%) | Thickness (mil) |
| 26.1 | 20 | 0.25 |
| 26.2 | 60 | 0.75 |
| 26.3 | 20 | 0.25 |

Example 38

Formulation and Extrusion

An exemplary multi-layer film in accordance with certain aspects of the present disclosure is provided in the instant example. The multi-layer film in this example is a three layer co-extruded film. For purposes of illustration, each layer of the multi-layer film is numbered successively in reference to Table 43 to correlate the layer composition with the layer thickness. The instant example is provided to evaluate the properties of the exemplary multi-layer film.

Each of a first- and a second-seal layer (27.1, 27.3) comprises ExxonMobil™ Exceed™ XP8656 and ExxonMobil™ LDPE LD 306.57 as the base resins Ampacet 10090P was added as a slip agent, Polyfil ABC5000HC was added as an antiblock agent, and Ampacet 104355-N was added as an antistatic agent. The percentages by weight of the components were about:

| | |
|---|---|
| 54.25% | ExxonMobil ™ Exceed ™ XP8656 |
| 38% | ExxonMobil ™ LDPE LD 306.57 |
| 1.75% | Ampacet 10090P |
| 4% | Polyfil ABC5000HC |
| 2% | Ampacet 104355-N |

The resins, the slip agent, the antiblock, and the antistatic agent were added to an extruder hopper and combined via blending to provide a formulation. The formulation was then heated in the extruder to form a molten material.

A deformation-resistant layer (27.2) comprises Braskem INSPIRE™ 114 and ExxonMobil™ Exceed™ XP8656 as the base resins Ampacet 10090P was added as a slip agent and Ampacet 104355-N was added as an antistatic agent. The percentages by weight of the components were about:

| | |
|---|---|
| 50% | Braskem INSPIRE ™ 114 |
| 47.25% | ExxonMobil ™ Exceed ™ XP8656 |

-continued

| | |
|---|---|
| 1.75% | Ampacet 10090P |
| 1% | Ampacet 104355-N |

The resins, the slip agent, and the antistatic agent were added to an extruder hopper and combined via blending to provide a formulation. The formulation was then heated in the extruder to form a molten material.

The molten materials described above were co-extruded and blown to form multi-layer film 27 with a gauge of about 1.5 mils, a density of 0.916 g/cm$^3$, and with layer thicknesses as described in Table 43.

TABLE 43

| Target Layer Thicknesses | | |
|---|---|---|
| Layer | Thickness (%) | Thickness (mil) |
| 27.1 | 20 | 0.3 |
| 27.2 | 60 | 0.9 |
| 27.3 | 20 | 0.3 |

Example 39

Heat Seal Strength

Figure 5:
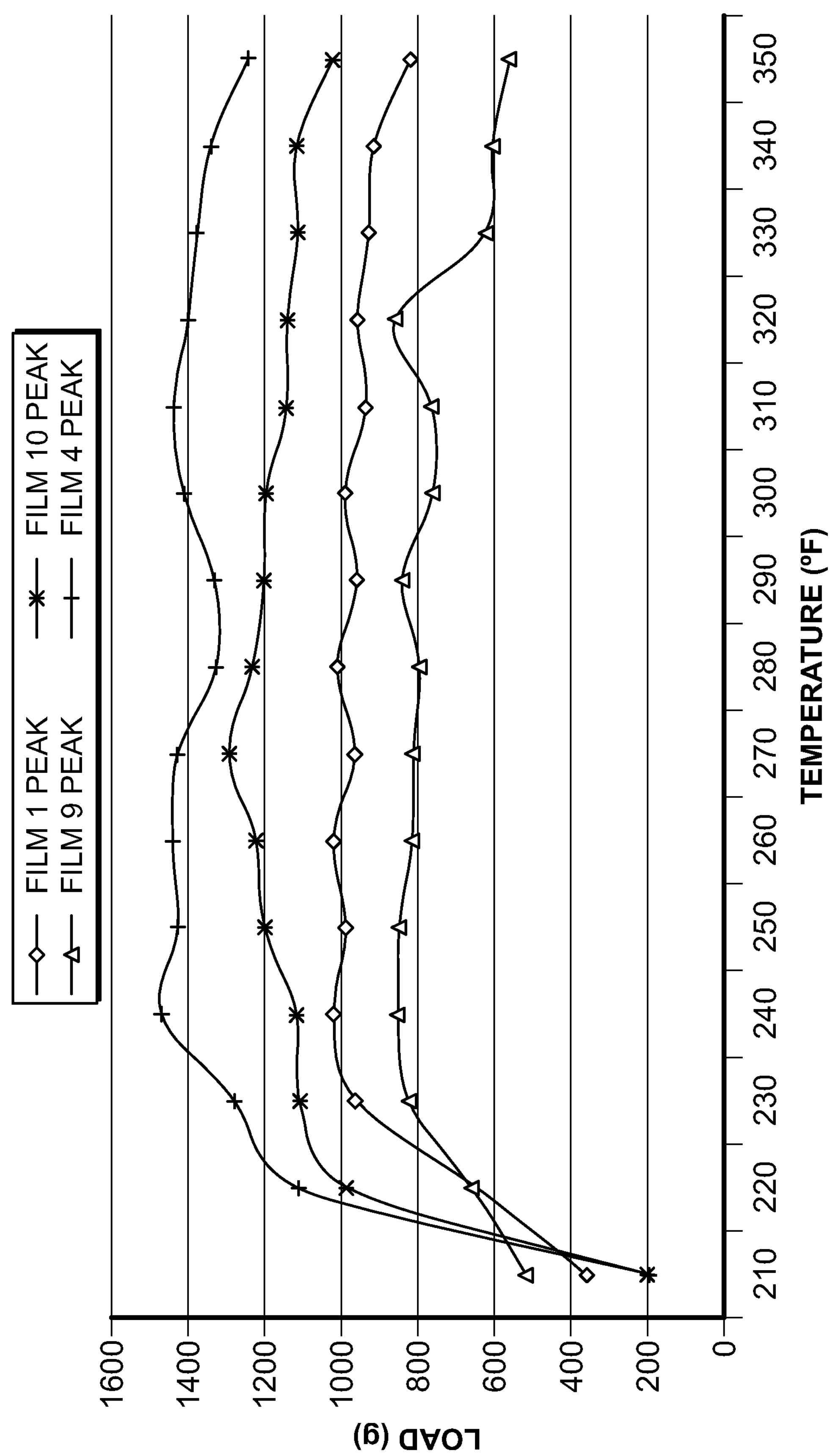
FIG. 5 is a graph similar to FIG. 3 showing heat-seal strength of exemplary multi-layer films.

Exemplary multi-layer films 1, 9, 10, and 4 were analyzed for heat seal strength. The exemplary multi-layer films were tested on a Hudson-Sharp Bagger with a jaw pressure of 60 PSI, a test speed of 30 cm/min, a dwell time of 1000 ms, and a cooling time of 10 s. The seal temperature was increased in 10° F. increments from 210° F. to 350° F. and the seal strength (g) was measured for each indicated temperature, as shown in Table 44 and FIG. 5. Peeling is defined as the two sealing layers separating at the sealing interface. Breaking is defined as the seal fracturing. Burn through is defined as when the jaws burn through the film.

TABLE 44

| Heat Seal values for exemplary multi-layer | | | | |
|---|---|---|---|---|
| Temp ° F. | Film 1 Load Peak (g) | Film 9 Load Peak (g) | Film 10 Load Peak (g) | Film 4 Load Peak (g) |
| 210 | 358* | 517* | 201* | 192* |
| 220 | 647* | 660* | 985* | 1110* |
| 230 | 962 | 824* | 1108* | 1278* |
| 240 | 1020 | 850* | 1117 | 1469 |
| 250 | 987 | 848 | 1201 | 1425 |
| 260 | 1022 | 814 | 1224 | 1441 |
| 270 | 965 | 812 | 1295 | 1427 |
| 280 | 1010 | 795 | 1232 | 1327 |
| 290 | 958 | 840 | 1200 | 1332 |
| 300 | 992 | 760 | 1198 | 1411 |
| 310 | 934 | 764 | 1142 | 1438 |
| 320 | 956# | 858 | 1141 | 1400 |
| 330 | 929** | 620 | 1112 | 1376 |
| 340 | 915** | 605** | 1117 | 1341 |
| 350 | 820** | 561** | 1021** | 1244 |

*denotes failure from peeling denotes failure from breaking

**denotes failure from burn through

Example 40

Heat Seal Strength

Figure 6:
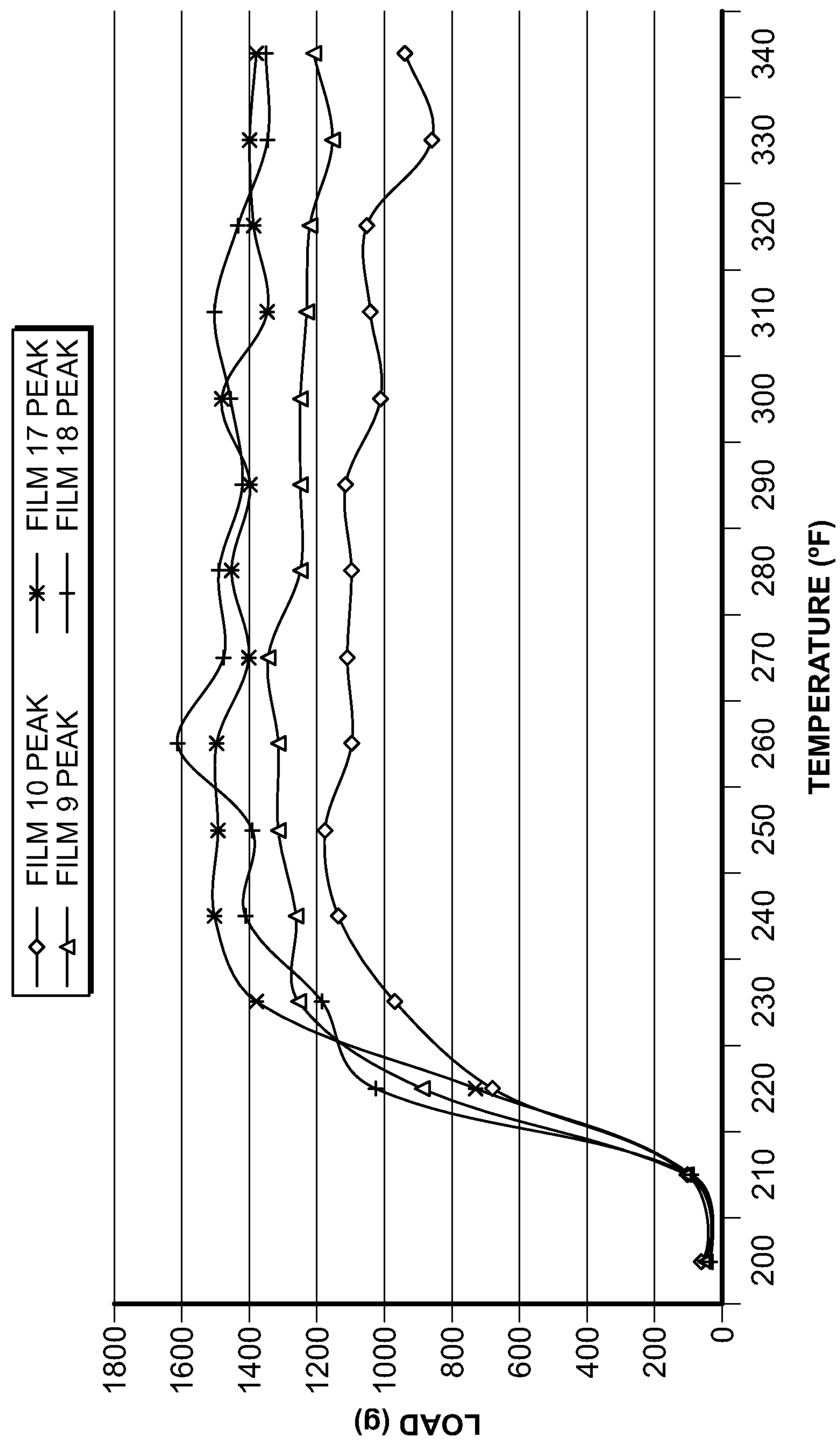
FIG. 6 is a graph similar to FIG. 3 showing heat-seal strength of exemplary multi-layer films.

Exemplary multi-layer films 9, 10, 17, and 18 were analyzed for heat seal strength. The exemplary multi-layer films were tested on a Hudson-Sharp Bagger with a jaw pressure of 60 PSI, a test speed of 30 cm/min, a dwell time of 1000 ms, and a cooling time of 10 s. The seal temperature was increased in 10° F. increments from 210° F. to 350° F. and the seal strength (g) was measured for each indicated temperature, as shown in Table 45 and FIG. 6. Peeling is defined as the two sealing layers separating at the sealing interface. Breaking is defined as the seal fracturing.

TABLE 45

| Heat Seal values for exemplary multi-layer | | | | |
|---|---|---|---|---|
| Temp ° F. | Film 9 Load Peak (g) | Film 10 Load Peak (g) | Film 17 Load Peak (g) | Film 18 Load Peak (g) |
| 200 | 39* | 32* | 22* | 22* |
| 210 | 107* | 104* | 73* | 84* |
| 220 | 677* | 888* | 730* | 1022* |
| 230 | 970* | 1254* | 1378* | 1185* |
| 240 | 1139* | 1260 | 1503 | 1409* |
| 250 | 1175 | 1319 | 1494 | 1394* |
| 260 | 1096 | 1315 | 1498 | 1609 |
| 270 | 1112 | 1346 | 1400 | 1478 |
| 280 | 1101 | 1245 | 1455 | 1492 |
| 290 | 1115 | 1250 | 1400 | 1423 |
| 300 | 1010 | 1251 | 1482 | 1456 |
| 310 | 1038 | 1234 | 1347 | 1502 |
| 320 | 1053 | 1219 | 1388 | 1434 |
| 330 | 858# | 1154 | 1400 | 1347 |
| 340 | 938# | 1211# | 1381 | 1355 |

*denotes failure from peeling denotes failure from breaking

Example 41

Heat Seal Strength

Figure 7:
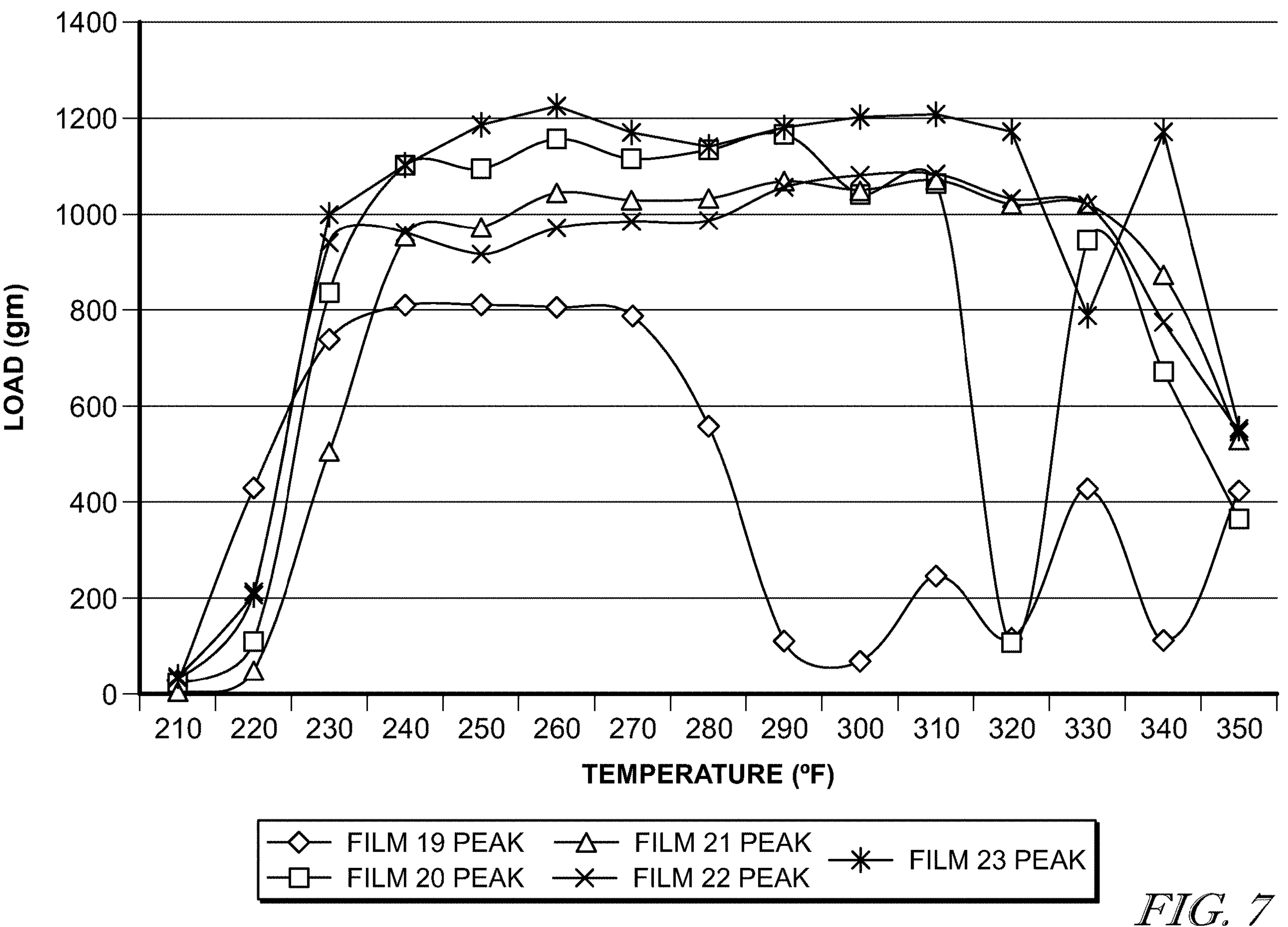
FIG. 7 is a graph similar to FIG. 3 showing heat-seal strength of exemplary multi-layer films.

Exemplary multi-layer films 19, 20, 21, 22, and 23 were analyzed for heat seal strength. The exemplary multi-layer films were tested on a Hudson-Sharp Bagger with a jaw pressure of 60 PSI, a test speed of 30 cm/min, a dwell time of 1000 ms, and a cooling time of 10 s. The seal temperature was increased in 10° F. increments from 210° F. to 350° F. and the seal strength (g) was measured for each indicated temperature shown in FIG. 7.

The invention claimed is:

1. A package comprising a bag formed to include an interior product storage region, and a first closure located on a first end of the bag, wherein the bag is formed of a multi-layer film including a first-seal layer, a second-seal layer, and a deformation-resistant layer extending between and interconnecting the first-seal layer and the second-seal layer, and the multi-layer film is configured to maximize a heat seal temperature range used to form the first closure and to minimize deformation of the bag so that an outer surface of the package remains uninterrupted during handling of the package;

wherein the deformation-resistant layer comprises about 45% by weight to about 75% by weight polypropylene impact copolymer; and wherein the multi-layer film has a slow puncture (¼") performance of about 1,300 gf to about 2,500 gf as measured by ASTM F1306.

2. The package of claim 1, wherein the deformation-resistant layer comprises a metallocene linear low density polyethylene (mLLDPE).

3. The package of claim 2, wherein the heat seal temperature range spans at least at least 120° F.

4. The package of claim 3, wherein the heat seal temperature range is about 210° F. to about 360° F.

5. The package of claim 1, wherein the deformation-resistant layer comprises an mLLDPE, and wherein the multi-layer film has a dart drop performance of about 150 g to about 350 g as measured by ASTM D1709.

6. The package of claim 1, wherein the deformation-resistant layer comprises about 5% by weight to about 55% by weight metallocene polyethylene copolymer.

7. The package of claim 1, wherein the heat seal temperature range spans at least at least 120° F.

8. The package of claim 7, wherein the heat seal temperature range is about 270° F. to about 400° F.

9. The package of claim 8, wherein the deformation-resistant layer comprises an mLLDPE.

10. The package of claim 1, wherein the first closure has a seal strength in a range of about 300 g to about 1,700 g.

11. The package of claim 1, wherein the multi-layer film has a dart drop performance of about 150 g to about 350 g as measured by ASTM D1709.

12. A multi-layer film comprising a first-seal layer, a second-seal layer located in spaced-apart relation to the first-seal layer, and a deformation-resistant layer arranged to extend between and interconnect the first-seal layer and the second-seal layer, wherein the deformation-resistant layer is configured to minimize deformation of the multi-layer film during handling so that an outer surface of the multi-layer film remains uninterrupted;

wherein the deformation-resistant layer comprises about 45% by weight to about 75% by weight polypropylene impact copolymer; and wherein the multi-layer film has a slow puncture (¼") performance of about 1,300 gf to about 2,500 gf as measured by ASTM F1306.

13. The multi-layer film of claim 12, wherein the deformation-resistant layer comprises a metallocene linear low density polyethylene (mLLDPE).

14. The multi-layer film of claim 13, wherein each of the first seal layer and the second-seal layer independently comprises a metallocene polyethylene copolymer, a polyethylene-EVA copolymer, or a mixture thereof.

15. A method of making a package, the method comprising providing a multi-layer film comprising a first-seal layer, a second-seal layer, and a deformation-resistant layer extending between and interconnecting the first-seal layer and the second-seal layer, and the multi-layer film, forming a bag using the multi-layer film, and sealing the bag to form a closure on the bag to establish the package, wherein the sealing step is performed at a temperature selected from a range of about 230° F. to about 400° F. and wherein the deformation-resistant layer comprises a polypropylene impact copolymer;

wherein the polypropylene impact copolymer is about 45% by weight to about 75% by weight of the deformation-resistant layer; and wherein the multi-layer film has a slow puncture (¼") performance of about 1,300 gf to about 2,500 gf as measured by ASTM F1306.

16. The method of claim 15, wherein the step of heat sealing is performed for a dwell time of about 5 ms to about 100 ms.

* * * * *